United States Patent
Mao et al.

(10) Patent No.: US 11,726,096 B2
(45) Date of Patent: Aug. 15, 2023

(54) FAST PROTEIN SEQUENCING

(71) Applicant: Regeneron Pharmaceuticals, Inc., Tarrytown, NY (US)

(72) Inventors: Yuan Mao, Hartsdale, NY (US); Qiangwei Xia, Flushing, NY (US); Lichao Zhang, San Jose, CA (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 929 days.

(21) Appl. No.: 16/592,437

(22) Filed: Oct. 3, 2019

(65) Prior Publication Data

US 2020/0110094 A1   Apr. 9, 2020

Related U.S. Application Data

(60) Provisional application No. 62/741,155, filed on Oct. 4, 2018.

(51) Int. Cl.
| | |
|---|---|
| *G01N 33/68* | (2006.01) |
| *G16B 20/00* | (2019.01) |
| *G16B 30/00* | (2019.01) |
| *C07K 1/12* | (2006.01) |
| *C07K 1/14* | (2006.01) |
| *C07K 16/06* | (2006.01) |

(52) U.S. Cl.
CPC ......... *G01N 33/6818* (2013.01); *C07K 1/128* (2013.01); *C07K 1/14* (2013.01); *C07K 16/065* (2013.01); *G01N 33/6851* (2013.01); *G16B 20/00* (2019.02); *G16B 30/00* (2019.02); *C07K 2317/41* (2013.01); *C12Y 304/23001* (2013.01); *C12Y 304/23018* (2013.01)

(58) Field of Classification Search
CPC ........ C07K 16/065; C07K 1/128; C07K 1/14; C07K 2317/41; C12Y 304/23001; C12Y 304/23018; G01N 33/6818; G01N 33/6821; G01N 33/6848; G01N 33/6851; G16B 20/00; G16B 30/00
See application file for complete search history.

(56) References Cited

U.S. PATENT DOCUMENTS

| | | | |
|---|---|---|---|
| 2005/0153380 A1* | 7/2005 | Everett | G01N 33/6848 435/7.92 |
| 2010/0316613 A1* | 12/2010 | Upton | C12N 5/0606 435/405 |
| 2017/0261513 A1 | 9/2017 | Kang et al. | |

FOREIGN PATENT DOCUMENTS

| | | |
|---|---|---|
| EP | 2081025 A1 | 7/2009 |
| WO | WO2004067551 A2 | 8/2004 |
| WO | WO2004081535 A2 | 9/2004 |
| WO | WO2011101370 A1 | 8/2011 |
| WO | WO2015051310 A2 | 4/2015 |
| WO | WO2016018978 A1 | 2/2016 |
| WO | WO2017210104 A2 | 12/2017 |

OTHER PUBLICATIONS

Norris et al. Analysis of Enzyme Kinetics Using Electrospray Ionization Mass Spectrometry and Multiple Reaction Monitoring: Fucosyltransferase V.Biochemistry 2001, vol. 40, No. 13, pp. 3774-3779. (Year: 2001).*
Chen. Rapid protein identification using direct infusion nanoelectrospray ionization mass spectrometry. Proteomics, 2006, vol. 6, pp. 16-25. (Year: 2006).*
Mao et al. Fast protein sequencing of monoclonal antibody by real-time digestion on emitter during nanoelectrospray. MABS 2019, vol. 11, No. 4, pp. 767-778. (Year: 2019).*
Cardenas M.S. et al,: "On-Line Derivatization of Peptides for Improved Sequence Analysis by Micro-Column Liquid Chromatography Coupled with Electrospray Ionization—Tandem Mas S. Spectrometry," Rapid Communications in Mass Spectrometry, John Wiley & Sons, GB, vol. 11, No. 12, Jan. 1, 1997, pp. 1271-1278.
European Search Report Application No. 19 20 1518, dated Feb. 18, 2020.
Zhao C et al.: "Integration of an on-line protein digestion microreactor to a nanoelectrospray emitter for peptide mapping", Analytical Biochemistry, Academic Press, Amsterdam, NL, vol. 359, No. 2, Dec. 15, 2006 (Dec. 15, 2006), pp. 167-175, XP024942239, ISSN: 0003-2697, DOI: 10.1016/J.AB.2006.09.005.

* cited by examiner

*Primary Examiner* — Marcela M Cordero Garcia
(74) *Attorney, Agent, or Firm* — Kramer Levin Naftalis & Frankel LLP

(57) ABSTRACT

Methods of sequencing a protein using a novel digestion-on-emitter technology are provided.

28 Claims, 16 Drawing Sheets

Specification includes a Sequence Listing.

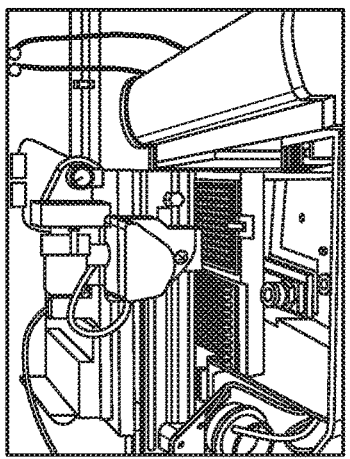
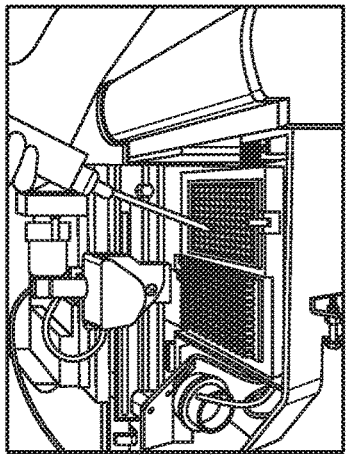
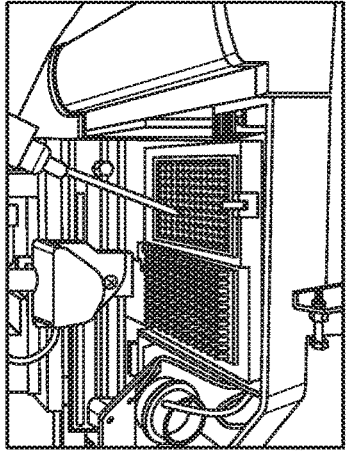
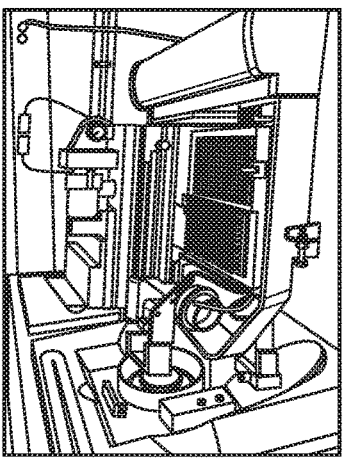
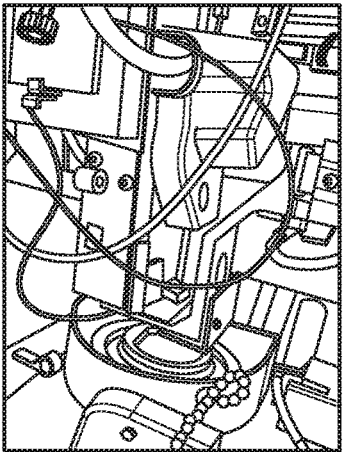
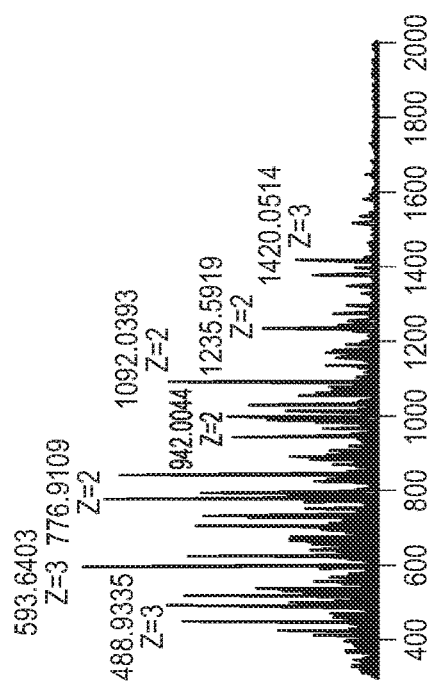
FIG. 2

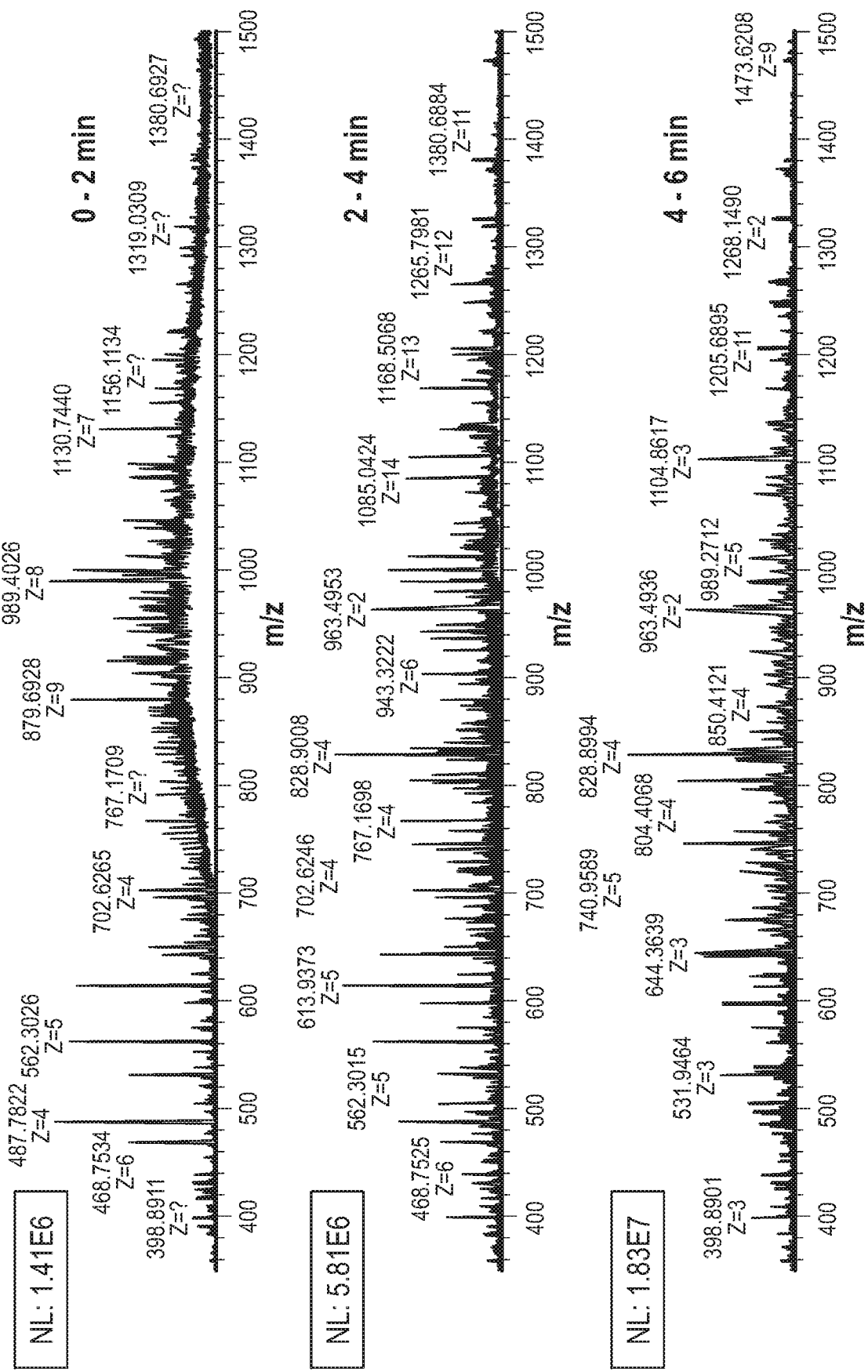
FIG. 3, Continued

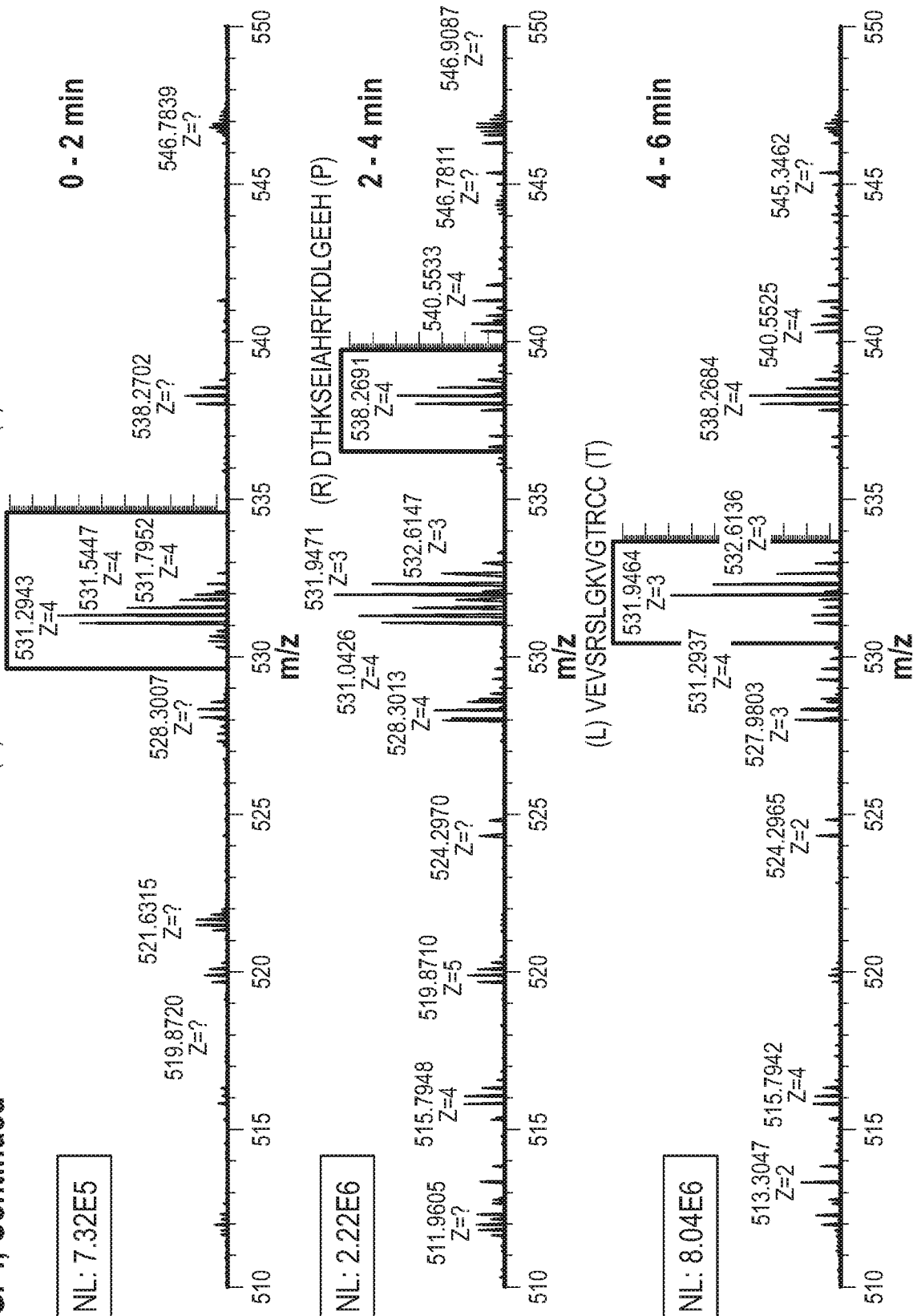
FIG. 4, Continued

FIG. 5

ProXIII/BSA
w/w, 1:1
61.3%

ProXIII/BSA
w/w, 1:5
94.1%

ProXIII/BSA
w/w, 1:10
85.2%

FIG. 7

MOPC21 IgG1 Heavy Chain 75.6%
```
DVQLVESGGG LVQPGGSRKL SCAASGFTFS SFGMHWVRQA PEKGLEWVAY ISSGSSTLHY60
ADTVKGRFTI SRDNPKNTLF LQMTSLRSED TAMYCARWG NYPYYAMDYW GQGTSVTVSS120
AKTTPPSVYP LAPGSAAQTN SMVTLGCLVK GYFPEPVTVT WNSGSLSSGV HTFPAVLQSD180
LYTLSSSVTV PSSTWPSETV TCNVAHPASS TKVDKKIVPR DCGCKPCICT VPEVSSVFIF240
PPKPKDVLTI TLTPKVTCVV VDISKDDPEV QFSWFVDDVE VHTAQTQPRE EQFNSTFRSV300
SELPIMHQDW LNGKEFKCRV NSAAFPAPIE KTISKTKGRP KAPQVYTIPP PKEQMAKDKVS360
LTCMITDFFP EDITVEWQWN GQPAENYKNT QPIMDTDGSY FVYSKLNVQK SNWEAGNTFT420
CSVLHEGLHN HHTEKSLSHS PG442
```

MOPC21 IgG1 Light Chain 95.3%
```
NIVMTQSPKS MSMSVGERVT LTCKASENVV TYVSWYQQKP EQSPKLLIYG ASNRYTGVPD60
RFTGSGSATD FTLTISSVQA EDLADYHCGQ GYSYPYTFGG GTKLEIKRAD AAPTVSIFPP120
SSEQLTSGGA SVVCFLNNFY PKDINVKWKI DGSERQNGVL NSWTDQDSKD STYSMSSTLT180
LTKDEYERHNS YTCEATHKTS TSPIVKSFNR NEC217
```

FIG. 8

NISTmAb IgG1κ
Heavy Chain
93.3%

QVTLRESGPA LVKPTQTLTL TCTFSGFSLS TAGMSVGWIR QPPGKALEWL ADIWWDDKKH$^{60}$
YNPSLKDRLT ISKDTSKNQV VLKVTNMDPA DTATYYCARD MIFNFYFDVW GQGTTVTVSS$^{120}$
ASTKGPSVFP LAPSSKSTSG GTAALGCLVK DYFPEPVTVS WNSGALTSGV HTFPAVLQSS$^{180}$
GLYSLSSVVT VPSSSLGTQT YICNVNHKPS NTKVDKRVEP KSCDKTHTCP PCPAPELLGG$^{240}$
PSVFLFPPKP KDTLMISRTP EVTCVVVDVS HEDPEVKFNW YVDGVEVHNA KTKPREEQYN$^{300}$
STYRVVSVLT VLHQDWLNGK EYKCKVSNKA LPAPIEKTIS KAKGQPREPQ VYTLPPSREE$^{360}$
MTKNQVSLTC LVKGFYPSDI AVEWESNGQP ENNYKTTPPV LDSDGSFFLY SKLTVDKSRW$^{420}$
QQGNVFSCSV MHEALHNHYT QKSLSLSPGK$^{450}$

NISTmAb IgG1κ
Light Chain
98.6%

DIQMTQSPST LSASVGDRVT ITCSASSRVG YMHWYQQKPG KAPKLLIYDT SKLASGVPSR$^{60}$
FSGSGSGTEF TLTISSLQPD DFATYYCFQG SGYPFTFGGG TKVEIKRTVA APSVFIFPPS$^{120}$
DEQLKSGTAS VVCLLNNFYP REAKVQWKVD NALQSGNSQE SVTEQDSKDS TYSLSSTLTL$^{180}$
SKADYEKHKV YACEVTHQGL SSPVTKSFNR GEC$^{213}$

FIG. 9

NISTmAb IgG1κ Heavy Chain 93.3%

QVTLRESGPA LVKPTQTLTL TCTFSGFSLS TAGMSVGWIR QPPGKALEWL ADIWWDDKKH⁶⁰
YNPSLKDRLT ISKDTSKNQV VLKVTNMDPA DTATYYCARD MIFNFYFDVW GQGTTVTVSS¹²⁰
ASTKGPSVFP LAPSSKSTSG GTAALGCLVK DYFPEPVTVS WNSGALTSGV HTFPAVLQSS¹⁸⁰
GLYSLSSVVT VPSSSLGTQT YICNVNHKPS NTKVDKRVEP KSCDKTHTCP PCPAPELLGG²⁴⁰
PSVFLFPPKP KDTLMISRTP EVTCVVVDVS HEDPEVKFNW YVDGVEVHNA KTKPREEQYN³⁰⁰
STYRVVSVLT VLHQDWLNGK EYKCKVSNKA LPAPIEKTIS KAKGQPREPQ VYTLPPSRE³⁶⁰
MTKNQVSLTC LVKGFYPSDI AVEWESNGQP ENNYKTTPPV LDSDGSFFLY SKLTVDKSRW⁴²⁰
QQGNVFSCSV MHEALHNHYT QKSLSLSPGK⁴⁵⁰

NISTmAb IgG1κ Light Chain 98.6%

DIQMTQSPST LSASVGDRVT ITCSASSRVG YMHWYQQKPG KAPKLLIYDT SKLASGVPSR⁶⁰
FSGSGSGTEF TLTISSLQPD DFATYYCFQG SGYPFTFGGG TKVEIKRTVA APSVFIFPPS¹²⁰
DEQLKSGTAS VVCLLNNFYP REAKVQWKVD NALQSGNSQE SVTEQDSKDS TYSLSSTLTL¹⁸⁰
SKADYEKHKV YACEVTHQGL SSPVTKSFNR GEC²¹³

FIG. 10

NISTmAb IgG1κ
Heavy Chain
79.6%

QVTLRESGPA LVKPTQTLTL TCTFSGFSLS TAGMSVGWIR QPPGKALEWL ADIWWDDKKH⁶⁰
YNPSLKDRLT ISKDTSKNQV VLKVTNMDPA DTATYYCARD MIFNFYFDVW GQGTTVTVSS¹²⁰
ASTKGPSVFP LAPSSKSTSG GTAALGCLVK DYFPEPVTVS WNSGALTSGV HTFPAVLQSS¹⁸⁰
GLYSLSSVVT VPSSSLGTQT YICNVNHKPS NTKVDKRVEP KSCDKTHTCP PCPAPELLGG²⁴⁰
PSVFLFPPKP KDTLMISRTP EVTCVVVDVS HEDPEVKFNW YVDGVEVHNA KTKPREEQYN³⁰⁰
STYRVVSVLT VLHQDWLNGK EYKCKVSNKA LPAPIEKTIS KAKGQPREPQ VYTLPPSREE³⁶⁰
MTKNQVSLTC LVKGFYPSDI AVEWESNGQP ENNYKTTPPV LDSDGSFFLY SKLTVDKSRW⁴²⁰
QQGNVFSCSV MHEALHNHYT QKSLSLSPGK⁴⁵⁰

NISTmAb IgG1κ
Light Chain
85.0%

DIQMTQSPST LSASVGDRVT ITCSASSRVG YMHWYQQKPG KAPKLLIYDT SKLASGVPSR⁶⁰
FSGSGSGTEF TLTISSLQPD DFATYYCFQG SGYPFTFGGG TKVEIKRTVA APSVFIFPPS¹²⁰
DEQLKSGTAS VVCLLNNFYP REAKVQWKVD NALQSGNSQE SVTEQDSKDS TYSLSSTLTL¹⁸⁰
SKADYEKHKV YACEVTHQGL SSPVTKSFNR GEC²¹³

FIG. 11

NISTmAb IgG1κ Heavy Chain 73.3%

QVTLRESGPA LVKPTQTLTL TCTFSGFSLS TAGMSVGWIR QPPGKALEWL ADIWWDDKKH⁶⁰
YNPSLKDRLT ISKDTSKNQV VLKVTNMDPA DTATYYCARD MIFNFYFDVW GQGTTVTVSS¹²⁰
ASTKGPSVFP LAPSSKSTSG GTAALGCLVK DYFPEPVTVS WNSGALTSGV HTFPAVLQSS¹⁸⁰
GLYSLSSVVT VPSSSLGTQT YICNVNHKPS NTKVDKRVEP KSCDKTHTCP PCPAPELLGG²⁴⁰
PSVFLFPPKP KDTLMISRTP EVTCVVVDVS HEDPEVKFNW YVDGVEVHNA KTKPREEQYN³⁰⁰
STYRVVSVLT VLHQDWLNGK EYKCKVSNKA LPAPIEKTIS KAKGQPREPQ VYTLPPSREE³⁶⁰
MTKNQVSLTC LVKGFYPSDI AVEWESNGQP ENNYKTTPPV LDSDGSFFLY SKLTVDKSRW⁴²⁰
QQGNVFSCSV MHEALHNHYT QKSLSLSPGK⁴⁵⁰

NISTmAb IgG1κ Light Chain 88.7%

DIQMTQSPST LSASVGDRVT ITCSASSRVG YMHWYQQKPG KAPKLLIYDT SKLASGVPSR⁶⁰
FSGSGSGTEF TLTISSLQPD DFATYYCFQG SGYPFTFGGG TKVEIKRTVA APSVFIFPPS¹²⁰
DEQLKSGTAS VVCLLNNFYP REAKVQWKVD NALQSGNSQE SVTEQDSKDS TYSLSSTLTL¹⁸⁰
SKADYEKHKV YACEVTHQGL SSPVTKSFNR GEC²¹³

FIG. 12

NISTmAb IgG1κ
Heavy Chain
89.6%

QVTLRESGPA LVKPTQTLTL TCTFSGFSLS TAGMSVGWIR QPPGKALEWL ADIWWDDKKH⁶⁰
YNPSLKDRLT ISKDTSKNQV VLKVTNMDPA DTATYYCARD MIFNFYFDVW GQGTTVTVSS¹²⁰
ASTKGPSVFP LAPSSKSTSG GTAALGCLVK DYFPEPVTVS WNSGALTSGV HTFPAVLQSS¹⁸⁰
GLYSLSSVVT VPSSSLGTQT YICNVNHKPS NTKVDKRVEP KSCDKTHTCP PCPAPELLGG²⁴⁰
PSVFLFPPKP KDTLMISRTP EVTCVVVDVS HEDPEVKFNW YVDGVEVHNA KTKPREEQYN³⁰⁰
STYRVVSVLT VLHQDWLNGK EYKCKVSNKA LPAPIEKTIS KAKGQPREPQ VYTLPPSREE³⁶⁰
MTKNQVSLTC LVKGFYPSDI AVEWESNGQP ENNYKTTPPV LDSDGSFFLY SKLTVDKSRW⁴²⁰
QQGNVFSCSV MHEALHNHYT QKSLSLSPGK⁴⁵⁰

NISTmAb IgG1κ
Light Chain
94.4%

DIQMTQSPST LSASVGDRVT ITCSASSRVG YMHWYQQKPG KAPKLLIYDT SKLASGVPSR⁶⁰
FSGSGSGTEF TLTISSLQPD DFATYYCFQG SGYPFTFGGG TKVEIKRTVA APSVFIFPPS¹²⁰
DEQLKSGTAS VVCLLNNFYP REAKVQWKVD NALQSGNSQE SVTEQDSKDS TYSLSSTLTL¹⁸⁰
SKADYEKHKV YACEVTHQGL SSPVTKSFNR GEC²¹³

FIG. 13

NISTmAb IgG1κ
Heavy Chain
93.3%

QVTLRESGPA LVKPTQTLTL TCTFSGFSLS TAGMSVGWIR QPPGKALEWL ADIWWDDKKH[60]
YNPSLKDRLT ISKDTSKNQV VLKVTNMDPA DTATYYCARD MIFNFYFDVW GQGTTVTVSS[120]
ASTKGPSVFP LAPSSKSTSG GTAALGCLVK DYFPEPVTVS WNSGALTSGV HTFPAVLQSS[180]
GLYSLSSVVT VPSSSLGTQT YICNVNHKPS NTKVDKRVEP KSCDKTHTCP PCPAPELLGG[240]
PSVFLFPPKP KDTLMISRTP EVTCVVVDVS HEDPEVKFNW YVDGVEVHNA KTKPREEQYN[300]
STYRVVSVLT VLHQDWLNGK EYKCKVSNKA LPAPIEKTIS KAKGQPREPQ VYTLPPSREE[360]
MTKNQVSLTC LVKGFYPSDI AVEWESNGQP ENNYKTTPPV LDSDGSFFLY SKLTVDKSRW[420]
QQGNVFSCSV MHEALHNHYT QKSLSLSPGK[450]

NISTmAb IgG1κ
Light Chain
97.2%

DIQMTQSPST LSASVGDRVT ITCSASSRVG YMHWYQQKPG KAPKLLIYDT SKLASGVPSR[60]
FSGSGSGTEF TLTISSLQPD DFATYYCFQG SGYPFTFGGG TKVEIKRTVA APSVFIFPPS[120]
DEQLKSGTAS VVCLLNNFYP REAKVQWKVD NALQSGNSQE SVTEQDSKDS TYSLSSTLTL[180]
SKADYEKHKV YACEVTHQGL SSPVTKSFNR GEC[213]

FAST PROTEIN SEQUENCING

SEQUENCE LISTING

The instant application contains a Sequence Listing which has been filed electronically in ASCII format and is hereby incorporated by reference in its entirety. Said ASCII copy, created on Nov. 13, 2019, is named 070816-01061_(10477-US)_SL.txt and is 18,876 bytes in size.

FIELD

The present invention generally pertains to a method of sequencing a protein.

BACKGROUND

Monoclonal antibodies and related products are one of the most rapidly growing classes of human therapeutics. A protein's sequence and structure can be critical to the therapeutic efficacy, storage, and immunogenicity properties of the protein. Further, during manufacture and storage, the sequence and structure of the protein may be affected and thus alter the protein's drug safety. This has generated a challenging demand to quickly and efficiently characterize proteins, such as, therapeutic monoclonal antibodies.

The first step in characterizing a protein is to determine the identity of the molecule by confirming its primary sequence. Several analytical techniques have been used for sequence confirmation of proteins, such as, N-terminal protein sequencing by Edman degradation technique and common peptide mapping. However, the Edman degradation technique can be time consuming and requires significant amounts of chemical reagents. Further, the common peptide mapping workflow comprises protein denaturation, reduction and alkylation of cysteine residues, proteolytic digestion, and liquid chromatography coupled with tandem mass spectrometry (LC-MS/MS) analysis, wherein the sample preparation itself often takes at least one day, which makes it difficult to accommodate faster monoclonal antibody sequencing requests.

Thus, there is a long felt need in the art for a method for rapid sequence analysis of proteins. In addition, demand for method of protein sequencing is increasing with the rapid development of monoclonal antibody-based pharmaceuticals. Considering the limitations of existing protein sequencing methods, an effective and efficient method for sequencing proteins using a novel digestion-on-emitter technology was developed.

SUMMARY

Growth in the development, manufacture and sale of monoclonal antibodies has led to an increasing demand for rapid characterization of therapeutic monoclonal antibodies. Current methods for antibody sequence confirmation (e.g., N-terminal Edman sequencing and traditional peptide mapping methods), however, struggle to meet this demand.

Embodiments disclosed herein satisfy the aforementioned demands by providing compositions, methods, and systems for the rapid characterization of proteins.

In some embodiments of the present invention, the weight ratio of the hydrolyzing agent to the substrate in the final sample can from can range from about 1:0.1 to about 1:50. In one exemplary embodiment, the weight ratio of the hydrolyzing agent to the substrate in the final sample is about 1:5. In another exemplary embodiment, the weight ratio of the hydrolyzing agent to the substrate in the final sample is about 1:10.

According to some embodiments of the present invention, the fast protein sequencing method can comprise digestion of at least one protein in a sample. The at least one protein can be digested with a solution of a hydrolyzing agent to form a final sample, wherein the hydrolyzing agent hydrolyzes the peptide bonds to fragment the at least one protein. The method of digestion of the at least one protein by the hydrolyzing agent could be enzymatic. In one exemplary embodiment, hydrolyzing agent used for a protein digestion is protease XIII or a biologically active fragment or homolog thereof.

To carry out the characterization of at least one protein, a setup comprising mass spectrometry can be used. For example, in certain embodiments of the present invention, the final sample containing the at least one protein and hydrolyzing agent is inserted as an electrospray into an orifice of a mass spectrometer, which is on-line with an electrospray infusion setup.

Traditional approaches to characterize a protein comprise carrying out protein sequencing by injecting the digested protein into an electrospray infusion setup—in conjunction with a mass spectrometer. This approach can lead to over-digestion or under-digestion of the protein and requires an extended duration of time for protein sequencing. To overcome digestion issues, the present invention, at least in part, discloses a new approach referenced as digestion-on-emitter. For example, according to some embodiments of the present invention, the final sample containing the at least one protein and the hydrolyzing agent is contacted on an electrospray emitter for a period of time (t) sufficient to produce digestion of the at least one protein on the electrospray emitter. In one exemplary embodiment, the period of time (t) sufficient to produce protein fragments and digestion of a protein on the electrospray emitter is less than about 20 minutes.

Further, the time required for sequencing at least one protein can be reduced by the use of an electrospray infusion setup coupled on-line with a tandem mass spectrometry setup. According to certain embodiments of the present invention, the fast protein sequencing method can comprise an electrospray infusion setup and tandem mass spectrometer, wherein the electrospray infusion setup can be on-line with a tandem mass spectrometer. The digestion-on-emitter technology and the coupling of the electrospray infusion setup with a mass spectrometer facilitate a real-time digestion on the spray emitter in parallel to a mass spectrometry data acquisition. The disclosed compositions, method, system and apparatuses help facilitate characterization of a protein much faster than alternative technologies, including N-terminal Edman sequencing and LC-MS/MS peptide mapping methods, and further have the potential to accommodate increasing demands from the biopharmaceutical industry for sequence confirmation of proteins.

An appropriate mass spectrometry setup can be used to characterize the at least one protein. In some embodiments of the present invention, the mass spectrometry setup employed to characterize the at least one protein is a tandem-in-time mass spectrometer. In one exemplary embodiment, a tandem-in-time mass spectrometer used to characterize the at least one protein is made by coupling a linear ion trap mass spectrometer to an orbitrap mass analyzer.

These, and other, aspects of the invention will be better appreciated and understood when considered in conjunction with the following description and the accompanying drawings. The following description, while indicating various embodiments and numerous specific details thereof, is given by way of illustration and not of limitation. Substitutions, modifications, additions, or rearrangements may be made within the scope of the embodiments, and the embodiments include all such substitutions, modifications, additions or rearrangements.

BRIEF DESCRIPTION OF THE DRAWINGS

FIG. 2 shows a typical workflow for the Fast Protein Sequencing (FPS) method according to one exemplary embodiment. The Fast Protein Sequencing (FPS) method can be carried out in six steps: 1) transfer of denatured and reduced protein sample to a sample vial; 2) addition of Protease XIII to the protein sample; 3) picking up infusion tip from infusion tip tray by infusion mandrel and movement to the sample plate to aspirate sample; 4) engagement of infusion tip to the nano ESI chip; 5) initiation of application of voltage to the infusion tip and ESI; and 6) acquiring mass spectrometry data for 30 minutes.

FIG. 4 discloses SEQ ID NOS 3-7, respectively, in order of appearance.

FIG. 5 shows sequence coverage maps of BSA at different enzyme to substrate ratios carried out by the FPS method according to one exemplary embodiment. The panels show the signal peptide (double underlined) and amino acid sequences identified by FPS method (underlined). FIG. 5 discloses SEQ ID NOS 8, 8 and 8, respectively, in order of appearance.

FIG. 7 shows a sequence coverage of heavy chain and light chain of IgG1 MOPC21 using FPS method (E/S ratio 1:1) carried out according to one exemplary embodiment. The panels show the glycosylation motif (NST) (double underlined) and amino acid sequences identified by FPS method (underlined). FIG. 7 discloses SEQ ID NOS 9-10, respectively, in order of appearance.

FIG. 8 shows a sequence coverage of heavy chain and light chain of NISTmAb using FPS method (E/S ratio 1:1) with Protease XIII carried out according to one exemplary embodiment. The panels show the glycosylation motif (NST) (double underlined) and amino acid sequences identified by FPS method (underlined). FIG. 8 discloses SEQ ID NOS 11-12, respectively, in order of appearance.

FIG. 9 shows a sequence coverage of heavy chain and light chain of NISTmAb using FPS method (E/S ratio 1:5) with Protease XIII carried out according to one exemplary embodiment. The panels show the glycosylation motif (NST) (double underlined) and amino acid sequences identified by FPS method (underlined). FIG. 9 discloses SEQ ID NOS 11-12, respectively, in order of appearance.

FIG. 10 shows a sequence coverage of heavy chain and light chain of NISTmAb using FPS method (E/S ratio 1:10) with Protease XIII carried out according to one exemplary embodiment. The panels show the glycosylation motif (NST) (double underlined) and amino acid sequences identified by FPS method (underlined). FIG. 10 discloses SEQ ID NOS 11-12, respectively, in order of appearance.

FIG. 11 shows a sequence coverage of heavy chain and light chain of NISTmAb using FPS method (E/S ratio 1:1) with pepsin carried out according to one exemplary embodiment. The panels show the glycosylation motif (NST) (double underlined) and amino acid sequences identified by FPS method (underlined). FIG. 11 discloses SEQ ID NOS 11-12, respectively, in order of appearance.

FIG. 12 shows a sequence coverage of heavy chain and light chain of NISTmAb using FPS method (E/S ratio 1:5) with pepsin carried out according to one exemplary embodiment. The panels show the glycosylation motif (NST) (double underlined) and amino acid sequences identified by FPS method (underlined). FIG. 12 discloses SEQ ID NOS 11-12, respectively, in order of appearance.

FIG. 13 shows a sequence coverage of heavy chain and light chain of NISTmAb using FPS method (E/S ratio 1:10) with pepsin carried out according to one exemplary embodiment. The panels show the glycosylation motif (NST) (double underlined) and amino acid sequences identified by FPS method (underlined). FIG. 13 discloses SEQ ID NOS 11-12, respectively, in order of appearance.

DETAILED DESCRIPTION

Figure 1:
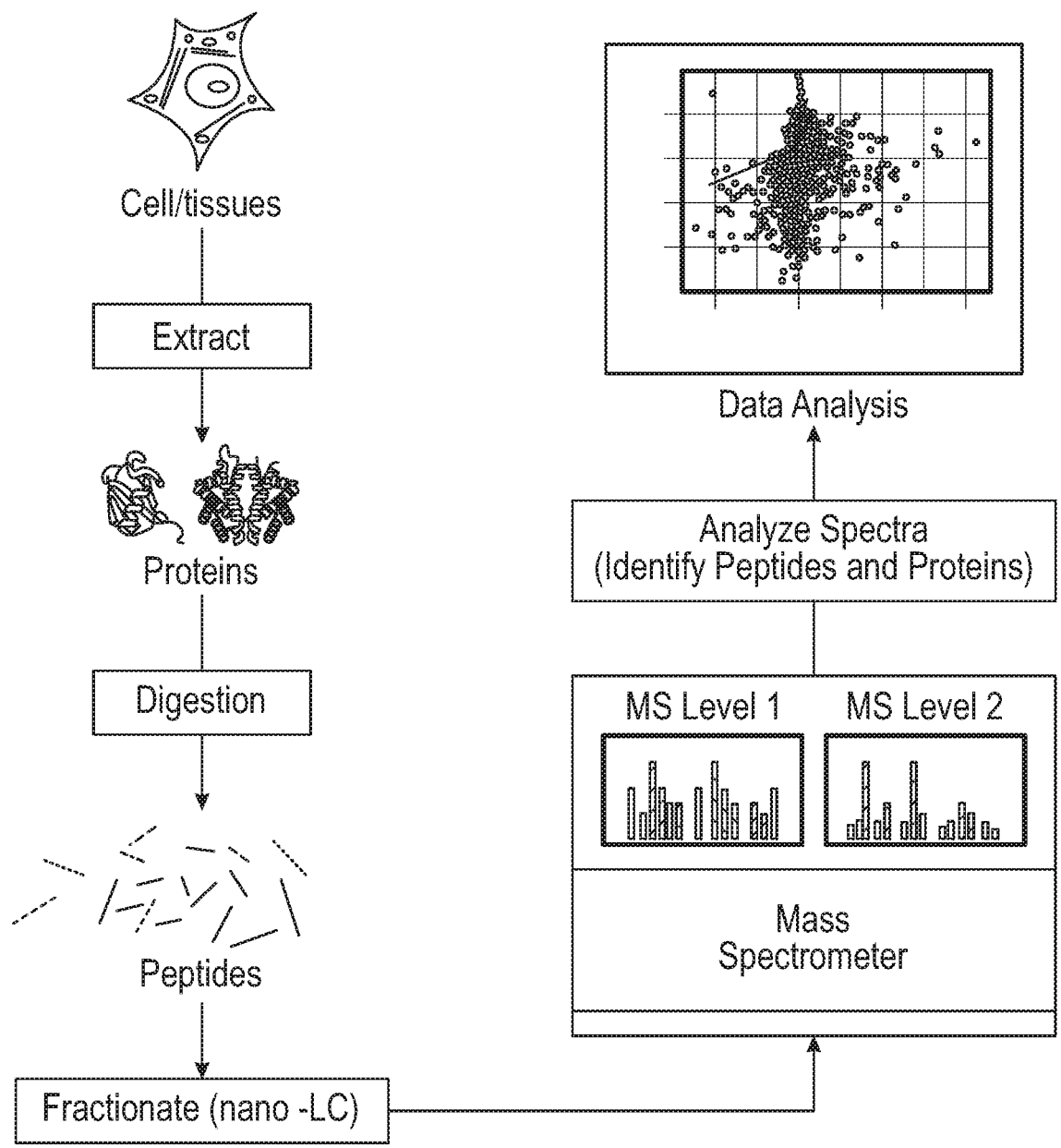
FIG. 1 represents a typical bottom-up proteomics workflow for a protein sequencing method

Over the past two decades, more than thirty monoclonal antibodies have successfully been used as therapeutics for the treatment of various human diseases (Sheridan C. "Fresh from the biologic pipeline—2009" Nat. Biotechnol. (2010) 28: 307-10; Reichert J M. "Antibody-based therapeutics to watch in 2011" mAbs. (2011) 3:76-99; Beck et al. "Strategies and challenges for the next generation of therapeutic antibodies." Nat. Rev. Immunol. (2010) 10:345-52).

As recombinant monoclonal antibody technology has matured, pharmaceutical companies are discovering and developing protein based therapeutics at an unprecedented rate (Nelson et al. "Development trends for human monoclonal antibody therapeutics." Nat. Rev. Drug Discov. (2010) 9:767-74; Martinez L J, "FDA Overview: An Overview of the Drug Approval Process. Research Initiative Treatment Action (RITA)" (2002) 8: 11-7). To match the unprecedented rate of development of protein-based therapeutics, techniques to sequence the protein also need to be developed. N-terminal protein sequencing by Edman degradation technique has been used in the pharmaceutical industry for decades to confirm monoclonal antibody identity. (Edman P. "A method for the determination of amino acid sequence in peptides." Arch. Biochem. (1949) 22:475). The Edman degradation technique is still considered a reliable technology, although it does have several disadvantages. For example, sample preparation for Edman degradation technique is time consuming and requires significant amounts of chemical reagents. Further, the sequencing method is a low-throughput technology that usually can only sequence one amino acid residue per hour (Henzel et al. "Protein identification: The origins of peptide mass fingerprinting." J. Am. Soc. Mass Spectrom. (2003) 14:931-42). Additionally, after fifty amino acid residues, the efficiency of Edman degradation technique declines significantly, making it unsuitable for sequencing large molecules such as monoclonal antibodies which have more than 1200 amino acid residues. (Berg et al. Biochemistry. 5th edition. New York: W H Freeman (2002) "Section 4.2, Amino Acid Sequences Can Be Determined by Automated Edman Degradation"). Moreover, the fact that the first several dozen N-terminal amino acid residues on monoclonal antibody molecules are conserved can make the Edman degradation technique even less effective for protein sequence confirmation.

A common peptide mapping workflow contains protein denaturation, reduction and alkylation of cysteine residues, proteolytic digestion, and liquid chromatography coupled with tandem mass spectrometry (LC-MS/MS) analysis. (Bondarenko et al. "Mass measurement and Top-Down HPLC/MS analysis of intact monoclonal antibodies on a hybrid linear quadrupole ion trap—Orbitrap mass spectrometer" J. Am. Soc. Mass Spectrom. (2009) 20: 1415-24); (Bourell et al. "Electrospray ionization mass spectrometry of recombinantly engineered antibody fragments" Anal. Chem. (1994) 66: 2088-2095); (Zhang et al. "Complete disulfide bond assignment of a recombinant immunoglobulin G4 monoclonal antibody" Anal. Biochem. (2002) 311:1-9); (Kroon et al. "Rapid profiling of carbohydrate glycoforms in monoclonal antibodies using MALDI/TOF mass spectrometry" J. Pharm. Biomed. Anal. (1995) 13: 1049-54); (Gibson and Biemann. "Strategy for the mass spectrometric verification and correction of the primary structures of proteins deduced from their DNA sequences" Proc. Natl. Acad. Sci. USA. (1984) 81:1956-1960); (Chelius et al. "Identification and characterization of deamidation sites in the conserved regions of human immunoglobulin gamma antibodies" Anal. Chem. (20050 77: 6004-11); (Kelleher N L. "Top-down proteomics. Anal. Chem. (2004) 76: 197A-203A); (Mao Y et al. "Top-down structure analysis of an intact monoclonal antibody by electron capture dissociation-Fourier transform ion cyclotron resonance-mass spectrometry" Anal. Chem. (2013) 85: 4239-46); (Tsybin et al. "Structural analysis of intact monoclonal antibodies by electron transfer dissociation mass spectrometry" Anal. Chem. (2011) 83: 8919-27); (Fornelli et al. "Analysis of Intact Monoclonal Antibody IgG1 by Electron Transfer Dissociation Orbitrap FTMS" Mol. Cell Proteomics. (2012) 11: 1758-67); (Barnes and Lim "Application of mass spectrometry for the structural characterization of recombinant protein pharmaceuticals" Mass Spectrom. Rev. (2007) 26: 370-88). Due to the rapid advancements in liquid chromatography and mass spectrometry instrumentation, this peptide mapping method can now routinely generate almost complete sequence coverage, and thus has become an effective approach for confirming monoclonal antibody identity. However, sample preparation in this approach takes at least one day, which can make it difficult to accommodate faster monoclonal antibody sequencing requests. Research efforts towards optimizing peptide mapping technology have been reported, such as the recent development of an on-line digestion system to reduce analysis time (Lopez-Ferrer et al. "Fast on-line digestion system for protein characterization" Anal Chem. (2008) 80: 8930-6 and Yuan et al. "Integrated platform for proteome profiling with combination of microreversed phase based protein and peptide separation via online solvent exchange and protein digestion" Anal. Chem. (2012) 84: 5124-32). However, both these methods require liquid chromatography for protein separation before protein characterization.

In a conventional bottom-up approach experiment, a protein is digested into small polypeptides to be characterized. The peptide mixture is then subjected to mass spectrometry analysis. Peptide identification can be further performed by comparing the tandem mass spectra derived from the polypeptide fragmentation with the theoretical mass spectra generated from in silico digestion of a protein. Protein inference is then accomplished by assigning peptide sequence to proteins. A typical workflow is represented in FIG. 1.

Exemplary embodiments of the present invention attempt to reduce the overall time required for characterizing a protein by employing digestion-on-emitter technology and on-line use of electrospray infusion setup with a tandem mass spectrometer.

Abbreviations and Acronyms

AMS accelerator mass spectrometry
CAD collision activated dissociation
CBP chitin binding protein
CDR complement determining regions
DTT dithiothreitol
E/S enzyme to substrate ratio
ESI electrospray ionization
FAB fast atom bombardment
FD field desorption
FDR false discovery rate
FPS fast protein sequencing
FR framework regions
FTICR Fourier transform ion cyclotron resonance
GST glutathione-S-transferase
HCD High-energy collision energy dissociation
IdeS immunoglobulin-degrading enzyme of Streptococcus pyogenes
IgG immunoglobulin
IMER immobilized enzyme digestion
KDa kilo Dalton
LC-MS liquid chromatography-mass spectrometry
LTQ linear trap quadrupole
mAb monoclonal antibody
MALDI matrix-assisted laser desorption/ionization
MBP maltose binding protein
mM millimolar
MS mass spectrometry
NP-LC normal phase liquid chromatography
OmpT outer membrane protein T
Q quadrupole mass filter
QIT quadrupole ion trap
RP-LC reversed phase liquid chromatography
TCEP tris(2-carboxyethyl)phosphine
TOF time-of-flight Unless defined otherwise, all technical and scientific terms used herein have the same meaning as commonly understood by one of ordinary skill in the art to which this invention belongs. Although any methods and materials similar or equivalent to those described herein can be used in the practice or testing, particular methods and materials are now described. All publications mentioned are hereby incorporated by reference.

The term "a" should be understood to mean "at least one"; and the terms "about" and "approximately" should be understood to permit standard variation as would be understood by those of ordinary skill in the art; and where ranges are provided, endpoints are included.

As used herein, the terms "include," "includes," and "including," are meant to be non-limiting and are understood to mean "comprise," "comprises," and "comprising," respectively.

Protein Digestion

As used herein, the term "protein" includes any amino acid polymer having covalently linked amide bonds. Proteins comprise one or more amino acid polymer chains, generally known in the art as "polypeptides". "Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof "Synthetic peptides or polypeptides' refers to a non-naturally occurring peptide or polypeptide. Synthetic peptides or polypeptides can be synthesized, for example, using an automated polypeptide synthesizer. Various solid phase peptide synthesis methods are known to those of skill in the art. A protein may contain one or multiple polypeptides to form a single functioning biomolecule. A protein can include any of bio-therapeutic proteins, recombinant proteins used in research or therapy, trap proteins and other chimeric receptor Fc-fusion proteins, chimeric proteins, antibodies, monoclonal antibodies, polyclonal antibodies, human antibodies, and bispecific antibodies. In another exemplary aspect, a protein can include antibody fragments, nanobodies, recombinant antibody chimeras, cytokines, chemokines, peptide hormones, and the like. Proteins may be produced using recombinant cell-based production systems, such as the insect bacculovirus system, yeast systems (e.g., *Pichia* sp.), mammalian systems (e.g., CHO cells and CHO derivatives like CHO-K1 cells). For a recent review discussing biotherapeutic proteins and their production, see Ghaderi et al., "Production platforms for biotherapeutic glycoproteins. Occurrence, impact, and challenges of non-human sialylation," (Biotechnol. Genet. Eng. Rev. (2012) 147-75). In some embodiments, proteins comprise modifications, adducts, and other covalently linked moieties. Those modifications, adducts and moieties include for example avidin, streptavidin, biotin, glycans (e.g., N-acetylgalactosamine, galactose, neuraminic acid, N-acetylglucosamine, fucose, mannose, and other monosaccharides), PEG, polyhistidine, FLAGtag, maltose binding protein (MBP), chitin binding protein (CBP), glutathione-S-transferase (GST) myc-epitope, fluorescent labels and other dyes, and the like. Proteins can be classified on the basis of compositions and solubility and can thus include simple proteins, such as, globular proteins and fibrous proteins; conjugated proteins, such as, nucleoproteins, glycoproteins, mucoproteins, chromoproteins, phosphoproteins, metalloproteins, and lipoproteins; and derived proteins, such as, primary derived proteins and secondary derived proteins.

As used herein, amino acids are represented by the full name thereof, by the three letter code corresponding thereto, or by the one-letter code corresponding thereto, as indicated in the following table:

| Full name | Three-letter code | One-letter code |
|---|---|---|
| alanine | Ala | A |
| arginine | Arg | R |
| asparagine | Asn | N |
| aspartic acid | Asp | D |
| cysteine | Cys | C |
| glutamic acid | Glu | E |

-continued

| Full name | Three-letter code | One-letter code |
|---|---|---|
| glutamine | Gln | Q |
| glycine | Gly | G |
| histidine | His | H |
| isoleucine | Ile | I |
| leucine | Leu | L |
| lysine | Lys | K |
| methionine | Met | M |
| phenylalanine | Phe | F |
| proline | Pro | P |
| serine | Ser | S |
| threonine | Thr | T |
| tryptophan | Trp | W |
| tyrosine | Tyr | Y |
| valine | Val | V |

As used herein, the term "amino acid' refers to both natural and synthetic amino acids, and both D- and L-amino acids. "Natural" or "Standard amino acid" refers to any of the twenty standard L-amino acids commonly found in naturally occurring peptides. "Nonstandard amino acid residue" refers to any amino acid, other than the standard amino acids, regardless of whether it is prepared synthetically or derived from a natural Source. As used herein, "synthetic amino acid" encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

The term "amino acid" can be used interchangeably with "amino acid residue" and may refer to a free amino acid and to an amino acid residue of a peptide. It will be apparent from the context in which the term is used whether it refers to a free amino acid or a residue of a peptide.

Amino acids have the following general structure:

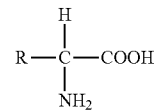

The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

Amino acids may be classified into four groups on the basis of the side chain R: (1) nonpolar amino acids, (2) polar uncharged amino acids, (3) polar-charged amino acids, and (4) aromatic amino acids.

As used herein, "non-polar amino acids" refers to a class of amino acids in which the variable R-groups have a neutral charge at pH 7.0 and are non-polar. Non-polar amino acids include, but are not limited to, the standard amino acids alanine, glycine, isoleucine, leucine, proline, and methionine.

As used herein, the term "polar amino acids" refers to a class of amino acids in which the variable R-groups have a neutral charge at pH 7.0 and are polar. Polar amino acids include, but are not limited to, the standard amino acids asparagine, cysteine, glutamine, serine, and threonine.

As used herein, the term "polar-charged amino acids" refers to a class of amino acids in which the variable R-groups have a charge at pH 7.0 and are polar. Polar amino acids include acidic and basic amino acids. The term "acidic" or "negatively charged amino acid" refers to amino acids in which the R groups have a net negative charge at pH 7.0, and include, but are not limited to, the standard amino acids glutamic acid and aspartic acid. The term "basic" or "positively charged amino acid" refers to amino acids in which the R groups have a net positive charge at pH 7.0, and include, but are not limited to, the standard amino acids lysine, arginine, and histidine.

As used herein, the term "aromatic amino acids" refers to a class of amino acids in which the variable R-groups are aromatic in nature, and include, but are not limited to, the standard amino acids phenylalanine, tyrosine, and tryptophan.

The term "antibody," as used herein includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_{H1}$, $C_{H2}$ and $C_{H3}$. Each light chain comprises a light chain variable region (abbreviated herein as LCVR or $V_L$) and a light chain constant region. The light chain constant region comprises one domain (C.sub.L1). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-big-ET-1 antibody (or antigen-binding portion thereof) may be identical to the human germline sequences, or may be naturally or artificially modified. An amino acid consensus sequence may be defined based on a side-by-side analysis of two or more CDRs. The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Prior to the addition of a hydrolyzing agent, a protein can be optionally prepared. This process of protein preparation includes denaturing the protein, reducing the protein, buffering the protein, and/or desalting the sample. These steps can be accomplished in any suitable manner as desired.

As used herein, the term "denaturing" refers to a process in which the three-dimensional shape of a molecule is changed from its native state without rupture of peptide bonds. Denaturation of the protein can be accomplished conventionally. Non-limiting methods of carrying out denaturation include heat, high or low pH, or exposure to chaotropic agents. Several chaotropic agents can be used to denature the protein. As used herein, a "chaotropic agent" is a substance which disrupts the structure of, and denatures proteins. Chaotropic solutes increase the entropy of the system by interfering with intramolecular interactions mediated by non-covalent forces such as hydrogen bonds, van der Waals forces, and hydrophobic effects. Non-limiting examples for chaotropic agents include butanol, ethanol, guanidinium chloride, lithium perchlorate, lithium acetate, magnesium chloride, phenol, propanol, sodium dodecyl sulfate, thiourea and urea.

As used herein, the term "reducing the protein" refers to the reduction of disulfide bridges in a protein. Non-limiting examples of the reducing agents used to reduce the protein are dithiothreitol (DTT), β-mercaptoethanol, Ellman's reagent, hydroxylamine hydrochloride, sodium cyanoborohydride, tris(2-carboxyethyl)phosphine hydrochloride (TCEP-HCl), or combinations thereof.

As used herein, the term "sample" refers to the product obtained after protein preparation which comprises at least one protein.

Several proteomic approaches are available that can be used to digest a protein. The sample preparation for such a digestion can be very laborious. A crucial step in such experiment is protein digestion, which is often the bottleneck in terms of time consumption. Therefore, sufficient gain can be achieved by accelerating the digestion process.

As used herein, the term "digestion" refers to hydrolysis of one or more peptide bonds of a protein. There are several approaches to carrying out digestion of a protein in a sample using an appropriate hydrolyzing agent, for example, enzymatic digestion or non-enzymatic digestion.

As used herein, the term "hydrolyzing agent" refers to any one or combination of a large number of different agents that can perform digestion of a protein. Non-limiting examples of hydrolyzing agents that can carry out enzymatic digestion include trypsin, endoproteinase Arg-C, endoproteinase Asp-N, endoproteinase Glu-C, outer membrane protease T (OmpT), immunoglobulin-degrading enzyme of *Streptococcus pyogenes* (IdeS), chymotrypsin, pepsin, thermolysin, papain, pronase, and protease from *Aspergillus saitoi*. Non-limiting examples of hydrolyzing agents that can carry out non-enzymatic digestion include the use of high temperature, microwave, ultrasound, high pressure, infrared, solvents (non-limiting examples are ethanol and acetonitrile), immobilized enzyme digestion (IMER), magnetic particle immobilized enzymes, and on-chip immobilized enzymes. For a recent review discussing the available techniques for protein digestion see Switazar et al., "Protein Digestion: An Overview of the Available Techniques and Recent Developments" (J. Proteome Research 2013, 12, 1067-1077). One or a combination of hydrolyzing agents can cleave peptide bonds in a protein or polypeptide, in a sequence-specific manner, generating a predictable collection of shorter peptides.

As used herein, the term "final sample" refers to the mixture of sample as described above with a hydrolyzing agent.

One of the widely accepted methods for digestion of proteins in a sample involves the use of proteases. Many proteases are available and each of them have their own characteristics in terms of specificity, efficiency, and optimum digestion conditions. Proteases refer to both endopeptidases and exopeptidases, as classified based on the ability of the protease to cleave at non-terminal or terminal amino acids within a peptide. Alternatively, proteases also refer to the six distinct classes—aspartic, glutamic, and metalloproteases, cysteine, serine, and threonine proteases, as classified on the mechanism of catalysis. The terms "protease" and "peptidase" are used interchangeably to refer to enzymes which hydrolyze peptide bonds.

Proteases can also be classified into specific and non-specific proteases. As used herein, the term "specific protease" refers to a protease with an ability to cleave the peptide substrate at a specific amino acid side chain of a peptide.

As used herein, the term "non-specific protease" refers to a protease with a reduced ability to cleave the peptide substrate at a specific amino acid side chain of a peptide. A cleavage preference may be determined based on the ratio of the number of a particular amino acid as the site of cleavage to the total number of cleaved amino acids in the protein sequences.

Conventional proteomic strategies employing protein digestion require longer periods of time to permit digestion. Although the sample preparation process can be automated, the digestion step remains a bottleneck in terms of time consumption.

As used herein, the term "period of time to permit digestion" refers to period of digestion time in order for the protein to be exposed in a time-controlled manner to the hydrolyzing agent. One of ordinary skill in the art can determine the digestion times based on factors such as the protein being characterized, the hydrolyzing agent being used, the temperature of incubation being used and the weight ratio of the hydrolyzing agent to the protein.

As used herein, the term "enzyme to substrate ratio" or "E/S" refers to the weight ratio of the enzymatic hydrolyzing agent to the protein. The enzyme to substrate ratio is an important parameter which affects protein sequence coverage and the time require to permit digestion of the protein. When the enzyme to substrate ratio is unsuitably high, the correspondingly high digestion rate will not allow sufficient time for the peptides to be analyzed by mass spectrometer, and sequence coverage will be compromised. On the other hand, a low E/S ratio would need long digestion and thus long data acquisition time. The enzyme to substrate ratio can range from about 1:0.5 to about 1:50.

It is understood that the present invention is not limited to any of the aforesaid protein(s), protein preparation method, or hydrolyzing agent(s), and that any protein(s), hydrolyzing agent(s), or protein preparation method can be selected by any suitable means.

Digestion-On-Emitter

As described in FIG. 1, in a conventional proteomics experiment, a protein is digested before it is analyzed by a tandem mass spectrometer. In some embodiments of the present invention, the fast protein sequencing method performs a real-time monitoring of protein digestion, which provides a unique view of a region of the protein. Real-time monitoring can be performed by contacting the final sample containing the protein and hydrolyzing agent to an electrospray emitter which is a part of an electrospray setup for the tandem mass spectrometer. Accordingly, the technology described herein is referred to as "digestion-on-emitter," since the digestion of the protein occurs on the emitter. The PFS proteomics approach according to one exemplary embodiment is described in FIG. 2.

As used herein, the term "mass spectrometer" refers to a device capable of detecting specific molecular species and accurately measuring their masses. The term is meant to include any molecular detector into which a polypeptide or peptide may be eluted for detection and/or characterization. A mass spectrometer consists of three major parts: the ion source, the mass analyzer, and the detector. The role of the ion source is to create gas phase ions. Analyte atoms, molecules, or clusters can be transferred into gas phase and ionized either concurrently (as in electrospray ionization). The choice of ion source depends on the application.

As used herein, the term "electrospray ionization" or "ESI" refers to the process of spray ionization in which either cations or anions in solution are transferred to the gas phase via formation and desolvation at atmospheric pressure of a stream of highly charged droplets that result from applying a potential difference between the tip of the electrospray needle containing the solution and a counter electrode. There are three major steps in the production of gas-phase ions from electrolyte ions in solution. These are: (a) production of charged droplets at the ES infusion tip; (b) shrinkage of charged droplets by solvent evaporation and repeated droplet disintegrations leading to small highly charged droplets capable of producing gas-phase ions; and (c) the mechanism by which gas-phase ions are produced from very small and highly charged droplets. Stages (a)-(c) generally occur in the atmospheric pressure region of the apparatus.

As used herein, the term "electrospray infusion setup" refers to an electrospray ionization system that is compatible with a mass spectrometer used for mass analysis of protein. In an electrospray ionization, an electrospray needle has its orifice positioned close to the entrance orifice of a spectrometer. A sample, containing the protein of interest, can be pumped through the syringe needle. An electric potential between the syringe needle orifice and an orifice leading to the mass analyzer forms a spray ("electrospray") of the solution. The electrospray can be carried out at atmospheric pressure and provides highly charged droplets of the solution. The electrospray infusion setup can include an electrospray emitter, nebulization gas, and/or a ESI power supply. The setup can optionally be automated to carry out sample aspiration, sample dispensing, sample delivery, and/or for spraying the sample. The term "nanoelectrospray" or "nanospray" as used herein refers to electrospray ionization at a very low solvent flow rate, typically hundreds of nanoliters per minute of sample solution or lower, often without the use of an external solvent delivery. The electrospray infusion setup forming a nanoelectrospray can use a static nanoelectrospray emitter or a dynamic nanoelectrospray emitter. A static nanoelectrospray emitter performs a continuous analysis of small sample (analyte) solution volumes over an extended period of time. A dynamic nanoelectrospray emitter uses a capillary column and a solvent delivery system to perform chromatographic separations on mixtures prior to analysis by the mass spectrometer.

As used herein, the term "electrospray emitter" or "electrospray needle" refers to the nanoelectrospray nozzle on the ESI Chip from which highly charged droplets are emitted in nanoelectrospray ionization.

As used herein, "mass analyzer" refers to a device that can separate species, that is, atoms, molecules, or clusters, according to their mass. Non-liming examples of mass analyzers that could be employed for fast protein sequencing are time-of-flight (TOF), magnetic/electric sector, quadrupole mass filter (Q), quadrupole ion trap (QIT), orbitrap, Fourier transform ion cyclotron resonance (FTICR), and also the technique of accelerator mass spectrometry (AMS).

As used herein, "mass-to-charge ratio" or "m/z" is used to denote the dimensionless quantity formed by dividing the mass of an ion in unified atomic mass units by its charge number (regardless of sign). In general, the charge state depends on: the method of ionization (as electrospray ionization, ESI tends to promote multiple ionization, which is not as frequent in MALDI), peptide length (as longer peptides have more groups where additional protons can be attached (basic residues)), peptide sequence (as some amino acids (e.g., Arg or Lys) are more susceptible to ionization than others), the instrument settings, solvent pH, and solvent composition.

As used herein, the term "tandem mass spectrometry" refers to a technique where structural information on sample molecules is obtained by using multiple stages of mass selection and mass separation. A prerequisite is that the sample molecules can be transferred into gas phase and ionized intact and that they can be induced to fall apart in some predictable and controllable fashion after the first mass selection step. Multistage MS/MS, or MS$^n$, can be performed by first selecting and isolating a precursor ion (MS$^2$), fragmenting it, isolating a primary fragment ion (MS$^3$), fragmenting it, isolating a secondary fragment (MS$^4$), and so on as long as one can obtain meaningful information or the fragment ion signal is detectable. Tandem MS have been successfully performed with a wide variety of analyzer combinations. What analyzers to combine for a certain application can be determined by many different factors, such as sensitivity, selectivity, and speed, but also size, cost, and availability. The two major categories of tandem MS methods are tandem-in-space and tandem-in-time, but there are also hybrids where tandem-in-time analyzers are coupled in space or with tandem-in-space analyzers.

A tandem-in-space mass spectrometer comprise of an ion source, a precursor ion activation device, and at least two non-trapping mass analyzers. Specific m/z separation functions can be designed so that in one section of the instrument ions are selected, dissociated in an intermediate region, and the product ions are then transmitted to another analyzer for m/z separation and data acquisition.

In tandem-in-time mass spectrometer ions produced in the ion source can be trapped, isolated, fragmented, and m/z separated in the same physical device.

As used herein, the term "linear ion trap-Orbitrap hybrid mass spectrometer" refers to a hybrid system made by coupling a linear ion trap mass spectrometer to an orbitrap mass analyzer. A tandem in-time experiment using the linear ion trap-Orbitrap hybrid mass spectrometer begins with ejection of all ions except those within a selected, narrow m/z range from the LTQ. The selected ions are inserted into orbitrap and are fragmented most often by low-energy CID. All fragments within the m/z acceptance range of the trap will remain in the trap, and an MS-MS spectrum can be obtained. Similar hybrid systems can be used for fast protein sequencing, such as, but not limited to QIT-FTICR and Qq-FTICR.

Tandem mass spectrometry causes fragmentation of the precursor ion. There are many methods used to activate these ions which can result in different types of fragmentation and thus reveal different information about the structure and composition of the molecule. Non-limiting examples of such ion-activation methods are i-source decay, post-source decay, collision activated dissociation, photodissociation, blackbody infrared radiative dissociation, electron capture dissociation, electron transfer dissociation, and surface induced dissociation.

As used herein, the term "collision activated dissociation" or "CAD" refers to an ion activation technique wherein the precursor ions collide with gas atoms or molecules, such as nitrogen, argon, or helium, and fragment. In the collision, a part of the kinetic energy is converted into vibrational/rotational energy of the parent ion. If the internal energy gained is high enough, the precursor ion will fragment fast enough for the fragment ions to be observed in the mass spectrometer. Depending on the type of mass analyzer, either high-energy CAD (kiloelectronvolt collision energy) or low-energy CAD (<100 eV) is performed.

It is understood that the present invention is not limited to any of the aforesaid mass spectrometer or activation technique, and that any p mass spectrometer or activation technique can be selected by any suitable means.

Characterization of the Protein

The peptides identified by the mass spectrometer can be used as surrogate representatives of the intact protein and their post translational modifications. They can be used for protein characterization by correlating experimental and theoretical MS/MS data, the latter generated from possible peptides in a protein sequence database. The characterization includes, but is not limited to sequencing amino acids of the protein fragments, determining protein sequencing, determining protein de novo sequencing, locating post-translational modifications, or identifying post translational modifications, or comparability analysis, or combinations thereof.

As used herein, the term "protein de novo sequencing" refers to a procedure for determination of the amino acid sequence of a peptide without relying on the information gained from other sources. Due to the excellent sensitivity of mass spectrometry, this technique can provide vital information that is often beyond the capabilities of conventional sequencing methods.

As used herein, the term "protein sequence coverage" refers to the percentage of the protein sequence covered by identified peptides. The percent coverage is calculated by dividing the number of amino acids in all found peptides by the total number of amino acids in the entire protein sequence.

As used herein, the general term "post-translational modification" refers to covalent modifications that polypeptides undergo, either during (co-translational modification) or after (post-translational modification) their ribosomal synthesis. The various post-translational modifications include, but are not limited to, cleavage, N-terminal extensions, protein degradation, acylation of the N-terminus, biotinylation (acylation of lysine residues with a biotin), amidation of the C-terminal, glycosylation, iodination, covalent attachment of prosthetic groups, acetylation (the addition of an acetyl group, usually at the N-terminus of the protein), alkylation (the addition of an alkyl group (e.g. methyl, ethyl, propyl) usually at lysine or arginine residues), methylation, adenylation, ADP-ribosylation, covalent cross links within, or between, polypeptide chains, sulfonation, prenylation, Vitamin C dependent modifications (proline and lysine hydroxylations and carboxy terminal amidation), Vitamin K dependent modification wherein Vitamin K is a cofactor in the carboxylation of glutamic acid residues resulting in the formation of a γ-carboxyglutamate (a glu residue), glutamylation (covalent linkage of glutamic acid residues), glycylation (covalent linkage glycine residues), glycosylation (addition of a glycosyl group to either asparagine, hydroxylysine, serine, or threonine, resulting in a glycoprotein), isoprenylation (addition of an isoprenoid group such as farnesol and geranylgeraniol), lipoylation (attachment of a lipoate functionality), phosphopantetheinylation (addition of a 4'-phosphopantetheinyl moiety from coenzyme A, as in fatty acid, polyketide, non-ribosomal peptide and leucine biosynthesis), phosphorylation (addition of a phosphate group, usually to serine, tyrosine, threonine or histidine), and sulfation (addition of a sulfate group, usually to a tyrosine residue). The post-translational modifications that change the chemical nature of amino acids include, but are not limited to, citrullination (the conversion of arginine to citrulline by deimination), and deamidation (the conversion of glutamine to glutamic acid or asparagine to aspartic acid). The post-translational modifications that involve structural changes include, but are not limited to, formation of disulfide bridges (covalent linkage of two cysteine amino acids) and proteolytic cleavage (cleavage of a protein at a peptide bond). Certain post-translational modifications involve the addition of other proteins or peptides, such as ISGylation (covalent linkage to the ISG15 protein (Interferon-Stimulated Gene)), SUMOylation (covalent linkage to the SUMO protein (Small Ubiquitin-related MOdifier)) and ubiquitination (covalent linkage to the protein ubiquitin).

As used herein, the term "analysis time" refers to the duration of time required for the preparation and sequencing of the protein. Analysis time could range from 10 minutes to 3 hours.

As used herein, the term "database" refers to bioinformatic tools which provide the possibility of searching the uninterpreted MS-MS spectra against all possible sequences in the database(s). Non-limiting examples of such tools are Mascot (http://www.matrixscience.com), Spectrum Mill (http://www.chem.agilent.com), PLGS (http://www.waters.com), PEAKS (http://www.bioinformaticssolutions.com), Proteinpilot (http://download.appliedbiosystems.com/proteinpilot), Phenyx (http://www.phenyx-ms.com), Sorcerer (http://www.sagenresearch.com), OMS SA (http://www.pubchem.ncbi.nlm.nih.gov/omssa/), X!Tandem (http://www.thegpm.org/TANDEM/), Protein Prospector (http://www. http://prospector.ucsfedu/prospector/mshome.htm), Byonic (https://www.proteinmetrics.com/products/byonic) or Sequest (http://fields.scripps.edu/sequest).

Exemplary Embodiments

Embodiments disclosed herein provide compositions, methods, and systems for the rapid characterization of proteins in a sample.

In certain exemplary embodiments of the present invention, the fast protein sequencing method comprises mixing a hydrolyzing agent with a sample containing a protein to form a final sample. The hydrolyzing agent performs digestion (protein hydrolysis) of the protein by either an enzymatic or a non-enzymatic method. Non-limiting examples of hydrolyzing agents that can perform protein digestion by enzymatic method include protease from *Aspergillus saitoi*, elastase, subtilisin, protease XIII, pepsin, trypsin, Tryp-N, chymotrypsin, aspergillopepsin I, LysN protease (Lys-N), LysC endoproteinase (Lys-C), endoproteinase Asp-N (Asp-N), endoproteinase Arg-C (Arg-C), endoproteinase Glu-C (Glu-C) or outer membrane protein T (OmpT), immunoglobulin-degrading enzyme of *Streptococcus pyogenes* (IdeS), thermolysin, papain, pronase, V8 protease or biologically active fragments or homologs thereof or combinations thereof. In one exemplary embodiment, the hydrolyzing agent is a non-specific protease, such as, protease XIII, pepsin, or combinations thereof. The period of time to permit digestion can depend on the concentration of protein in the sample, concentration of hydrolyzing agent, conditions, and the weight ratio of hydrolyzing agent to the protein. The concentration of the solution containing hydrolyzing agent is about 0.1 μg/μL to about 100 μg/μL. In one embodiment, the concentration of the enzyme solution is about 0.1 μg/μL, or about 0.2 μg/μL, or 0.5 μg/μL, or about 1 μg/μL, or about 2 μg/μL, or about 3 μg/μL, or about 4 μg/μL, or about 5 μg/μL, or about 10 μg/μL, or about 15 μg/μL, or about 20 μg/μL, or about 25 μg/μL, or about 30 μg/μL, or about 35 μg/μL, or about 40 μg/μL, or about 45 μg/μL, or about 50 μg/μL, or about 60 μg/μL, or about 70 μg/μL, or about 80 μg/μL, or about 90 μg/μL, or about 100 μg/μL. The concentration of the protein in a sample can range from about 0.1 μg/μL to about 100 μg/μL. For example, the concentration of the protein in the sample is about 0.1 μg/μL, or about 0.2 μg/μL, or about 0.5 μg/μL, or about 1 μg/μL, or about 2 μg/μL, or about 3 μg/μL, or about 4 μg/μL, or about 5 μg/μL, or about 10 μg/μL, or about 15 μg/μL, or about 20 μg/μL, or about 25 μg/μL, or about 30 μg/μL, or about 35 μg/μL, or about 40 μg/μL, or about 45 μg/μL, or about 50 μg/μL, or about 60 μg/μL, or about 70 μg/μL, or about 80 μg/μL, or about 90 μg/μL, or about 100 μg/μL. In one exemplary embodiment, wherein the hydrolyzing agent perform protein digestion by an enzymatic method, the weight ratio of hydrolyzing agent (enzyme in this embodiment) to the protein, referred to as weight ratio (w/w) enzyme to substrate is from about 1:0.1 to about 1:50. For example, the enzyme to substrate ratio (w/w) can be about 1:0.5, or about 1:1, or about 1:2, or about 1:3, or about 1:4, or about 1:5, or about 1:10, or about 1:15, or about 1:20, or about 1:25, or about 1:30, or about 1:35, or about 1:40, or about 1:45, or about 1:50. In another exemplary embodiment, the fast protein sequencing method requires about less than an hour to permit digestion, for example, the fast protein sequencing method requires a period of time (t) of about 0.5 minute, or about 1 minute, or about 2 minutes, or about 3 minutes, or about 4 minutes, or about 5 minutes, or about 10 minutes, or about 12 minutes, or about 15 minutes, or about 18 minutes, or about 20 minutes, or about 25 minutes, or about 30 minutes, or about 40 minutes, or about 50 minutes, or about 60 minutes.

In certain embodiments of the present invention, the fast protein sequencing method comprises steps to prepare the sample containing the protein. The steps of preparing the sample containing the protein can include denaturation of the protein, reduction of the disulfide bonds in the protein and/or desalting. Denaturation changes the 3D structure of the protein from its natural state without rupturing the peptide bonds of the protein. The denaturation can be carried out at an acidic or basic pH. In one exemplary embodiment, the fast protein sequencing method comprises a step of denaturing the protein by subjecting the protein at an acidic pH, for example, at a the pH of about 0, or about 0.5, or about 1, or about 1.5, or about 2, or about 2.5, or about 3, or about 3.5, or about 4, or about 4.5, or about 5, or about 5.5, or about 6. In one exemplary embodiment, the fast protein sequencing method comprises a step of denaturing the protein by subjecting the protein at an basic pH, for example, at a pH of about 8, or about 8.5, or about 9, or about 9.5, or about 10, or about 10.5, or about 11, or about 11.5, or about 12, or about 12.5, or about 13, or about 13.5, or about 14. Further, denaturation can be carried out by using chaotropic agents. Non-limiting examples of chaotropic agents include butanol, ethanol, guanidinium chloride, lithium perchlorate, lithium acetate, magnesium chloride, phenol, propanol, sodium dodecyl sulfate, thiourea, or urea, or combinations thereof. Reducing the protein by reducing agents causes reduction of the disulfide bridges in a protein. Non-limiting examples of reducing agents include dithiothreitol (DTT), β-mercaptoethanol, Ellman's reagent, hydroxylamine hydrochloride, sodium cyanoborohydride, tris (2-carboxyethyl) phosphine hydrochloride (TCEP-HCl), or combinations thereof. Alternatively, a step of desalting can be performed on the protein to prepare the sample by suspending the protein in an appropriate agent, such as, 0.1-1% FA in water, 0.1-1% FA in methanol/water (50/50, v/v), 0.1-1% FA in ACN/water (50/50, v/v), ultra-pure water (Milli 18MΩ cm, or LC-MS grade bottled water). Finally, the protein can be desalted to form the sample. Non-limiting examples of methods of desalting include by using dialysis, ultrafiltration, desalting chromatography columns, gel filtration column, centrifugal ultra-filtration, or combinations thereof.

In certain embodiments of the present invention, the fast protein sequencing method comprises characterizing the protein by analyzing the final sample on an electrospray emitter by using a tandem mass spectrometer. A mass spectrometer can comprise an ion source, the mass analyzer, and the detector. The tandem mass spectrometer can be selected from MS/MS, $MS^3$, or $MS^4$. Non-limiting examples of mass spectrometers are time-of-flight (TOF), magnetic/electric sector, quadrupole mass filter (Q), quadrupole ion trap (QIT), orbitrap, Fourier transform ion cyclotron resonance (FTICR), or accelerator mass spectrometry (AMS). In one exemplary embodiment, the tandem mass spectrometer is a hybrid system comprising a linear ion trap-Orbitrap hybrid mass spectrometer. In one exemplary embodiment, the ion source for the mass spectrometer can be an electrospray infusion setup. Further, the mass analyzer for the mass analyzer can be selected from time-of-flight (TOF), magnetic/electric sector, quadrupole mass filter (Q), quadrupole ion trap (QIT), orbitrap, Fourier transform ion cyclotron resonance (FTICR), accelerator mass spectrometry (AMS), or combinations thereof. In one exemplary embodiment, the electrospray infusion setup is on-line with the mass spectrometer. The electrospray infusion setup may include an electrospray emitter, nebulization gas, and/or an ESI power supply. The electrospray emitter can have a carbon-coated infusion tip. The ESI power supply can apply a positive/negative voltage on the carbon-coated infusion tip of the electrospray emitter while the mass spectrometer sample orifice remains at 0 kV, generating an intense electrostatic field between the final sample in the emitter and the grounded orifice of the mass spectrometer and hence generates the electrospray. In one exemplary embodiment, a positive voltage is applied on the carbon-coated infusion tip of the electrospray emitter. The positive voltage applied on the carbon-coated infusion tip of the electrospray emitter can be selected from about 0.5 kV, about 1 kV, about 1.4 kV, about 2 kV, about 3 kV, or about 4 kV.

Several ion activation methods can be used for activation of precursor ions (refer to Sleno and Volmer, "Ion activation methods for tandem mass spectrometer" J. Mass Spectrom. (2004) 39(10): 1091-1112). In one exemplary embodiment of the present invention, the ion activation method for activation of precursor ions in tandem mass spectrometer can be either CAD (keV) or low energy CAD (<100 eV).

The spectra of the final sample from the tandem mass spectrometer can be used for protein inference. For example, in certain embodiments of the present invention, the fast protein sequencing method comprises characterizing the protein by comparing tandem mass spectra using MS/MS databases. Several databases exist which can be used for protein inference. For a review, refer to Knapp and Schutz ("Overview of tandem mass spectrometer (MS/MS) database search algorithms. Curr. Protoc. Protein Sci. (2007) 25.2.1.-25.2.19) and Zhang et al. ("Protein analysis by shotgun/bottom-up proteomics" Chem. Rev. (2013) 113(4): 2343-2394). Non-limiting examples of databases include Mascot, Spectrum Mill, PLGS, PEAKS, Proteinpilot, Phenyx, Sorcerer, OMSSA, X!Tandem, Protein Prospector, or Sequest, or combinations thereof.

Characterization of the protein can include protein sequencing, protein de novo sequencing, identifying post translational modifications, or comparability analysis, or combinations thereof.

The fast protein sequencing method used to characterize the protein in a sample can provide a protein sequence coverage of at least 60%. In some exemplary embodiments of the present invention, the method provides a protein sequence coverage of at least 60%, or at least 65%, or at least 70%, or at least 75%, or at least 80%, or at least 85%, or at least 90%, or at least 92%, or at least 94%, or at least 95%, or at least 96%, or at least 98%, or at least 99%.

In some exemplary embodiments of the present invention, the protein characterized by the fast protein sequencing method can include a therapeutic protein. The therapeutic protein can be selected from a recombinant protein, a trap protein, a globular protein, fibrous protein, an immunoglobulin, an antibody, human antibody, humanized antibody, bi-specific antibody, conjugated antibody, dimeric antibody, monoclonal antibody, a therapeutic antibody, an antibody fragment, Fab fragment (Fab), fragment, $F(ab^1)2$ fragment, scFv fragment, Fv fragment, dsFv fragment, dsFv antibody, dAb fragment, $Fd^1$ fragment, an isolated CDR region, triabody, tetrabody, linear antibody, single-drain antibody, multispecific antibody, or combinations thereof.

According to some embodiments of the present invention, the analysis time to prepare the sample containing the protein and to sequence the protein using the fast protein sequencing method can be less than about 3 hours. For example, the analysis time can be less than about 30 minutes, or less than about 40 minutes, or less than about 45 minutes, or less than about 50 minutes, or less than about 55 minutes, or less than about 60 minutes, or less than about 70 minutes, or less than about 80 minutes, or less than about 90 minutes, or less than about 120 minutes, or than about 150 minutes, or less than about 180 minutes.

All literature and patent-document citations herein are incorporated herein by reference in their entirety.

The present invention will be more fully understood by reference to the following Examples. They should not, however, be construed as limiting the scope of the invention.

EXAMPLES

Fast Protein Sequencing (FPS) Method.

FIG. 2 illustrates an exemplary experimental workflow of the fast protein sequencing method. After protein was denatured, reduced and desalted, the sample was transferred to a sample vial on Advion TriVersa NanoMate® which was mounted on Thermo LTQ Velos Orbitrap mass spectrometer (Lu et al. "Nanoelectrospray peptide mapping revisited: Composite survey spectra allow high dynamic range protein characterization without LCMS on an orbitrap mass spectrometer." Anal Chem. (2008) 80: 8930-6). Protease XIII was then added at the desired enzyme to substrate ratio (w/w). The enzyme and protein were mixed by pipetting up and down. The TriVersa NanoMate® infusion mode was triggered immediately afterwards. The infusion mandrel first moved to the infusion tip tray to pick up an infusion tip, then moved to the sample plate to aspirate the sample. The infusion tip was then engaged to the ESI chip. Subsequently, nanospray ESI and the LTQ Orbitrap data acquisition were triggered. Tandem mass spectrometry data were acquired for 30 minutes. The total time for sample preparation and data acquisition was approximately one hour.

Materials.

Bovine serum albumin, IgG1 Kappa murine myeloma (Clone Number MOPC 21), NISTmAb, pepsin and protease from *Aspergillus saitoi* (Type XIII) were purchased from Sigma (St. Louis, Mo., USA). Tris (2-carboxyethyl) phosphine hydrochloride (TCEP-HCl) and glacial acetic acid were purchased from Thermo Scientific (Newington, N.H.). Milli-Q Water was obtained from Millipore Milli-Q Advantage A10 Water Purification System (Billerica, Mass., USA). Trifluoroacetic Acid (TFA) and formic acid (FA) were purchased from Thermo Scientific (Newington, N.H.). Acetonitrile (Optima LC/MS) was purchased from Fisher Scientific (Suwanee, Ga.). MS compatible human protein extract prepared from human K562 cells was purchased from Promega (Madison, Wis., USA).

Example 1. Sequencing BSA by FPS Using Protease XIII 1.1 Protein Preparation.

A 1 µg/µL BSA stock solution was made with Milli-Q water. BSA stock solution (100 µg) was mixed with 1 µL of 1M acetic acid and 24, of 0.5M TCEP-HCl (final pH was 3). The mixture was incubated for 10 minutes at 80° C. The reduced sample was desalted with NanoSep 10K filter (Pall Life Sciences, Ann Arbor, USA) for 12 minutes and resuspended in 100 µL Milli-Q water.

1.2 Protease XIII Preparation.

A 10 µg/µL protease XIII stock solution was made with Milli-Q water.

1.3 Direct Infusion Mass Spectrometric Analysis.

MS mass analyses were performed using a linear ion trap-Orbitrap hybrid mass spectrometer (LTQ-Orbitrap Velos, Thermo Fisher Scientific, San Jose, Calif., USA) with a TriVersa NanoMate® (Advion Biosciences, Ithaca, USA) mounted in front. The TriVersa NanoMate was operated in the infusion mode. The TriVersa NanoMate was triggered once the protein and protease XIII were mixed. The infusion mandrel picked up an infusion tip from the infusion tip box and moved to the Eppendorf plate (Protein LowBind MTP 384/V-bottom, Eppendorf, Edison, N.J., USA) to aspirate 15 µL of sample. The infusion mandrel then engaged the infusion tip to the chip and a positive voltage (1.4 kV) was applied on the carbon-coated infusion tip while the mass spectrometer sample orifice remained at 0 kV. The very intense electrostatic field between the sample in the infusion tip and the grounded outside surface of the spray nozzle on the nano ESI chip generated the electrospray. The vacuum inside the mass spectrometer drove the positive ions towards the mass spectrometer. Mass analysis was completed using a method comprising full MS (resolution of 60,000 at m/z 400) acquired in the orbitrap, followed by 10 data-dependent CAD scans acquired in LTQ. Data-dependence parameters were set as follows: repeat count of 1, repeat duration of 120 s, 3 m/z precursor isolation window, charge state rejection for +1 precursor ions. The raw data were searched against protein database containing BSA with Proteome Discoverer 1.4 (Thermo Scientific).

1.4 Results.

Figure 3:
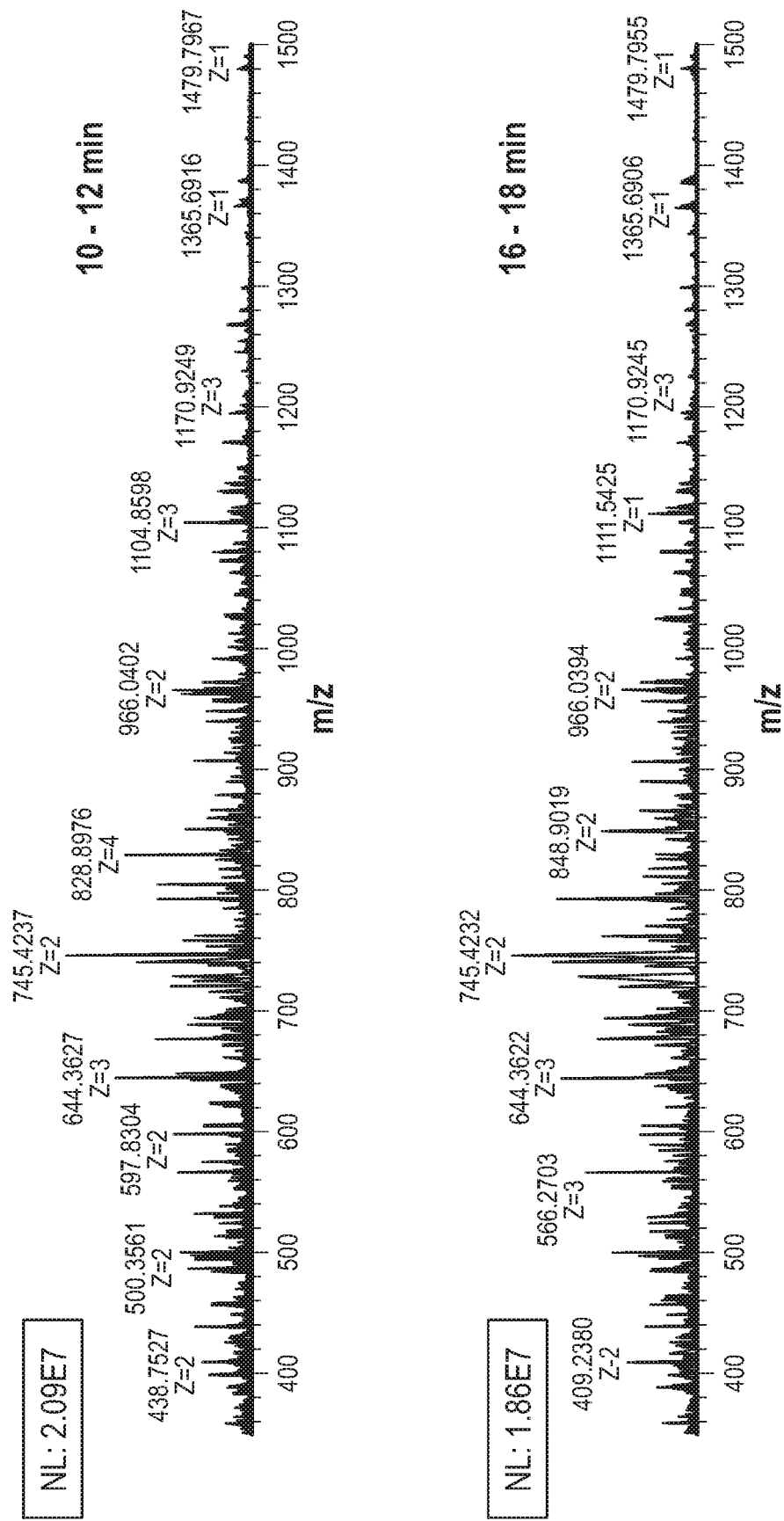
FIG. 3 shows the sequencing of Bovine serum albumin (BSA) carried out by the FPS method according to one exemplary embodiment. A full MS spectra of protease XIII digestion of BSA at various time points (E/S ratio 1:5) is displayed. Each panel shows the spectrum averaged over two minutes

As bovine serum albumin (BSA) is a protein standard for evaluating LC-MS/MS systems, in the initial stage of method development, BSA was treated with protease XIII using various weight ratios of enzyme to substrate (E/S) to provide the proof-of-principle. FIG. 3 shows the full MS spectra of protease XIII digestion of BSA at different time points (E/S ratio=1:5). Each panel in FIG. 3 shows the spectrum averaged over two minutes. It can be seen from the figure that in the first two minutes of the digestion, a majority of the peptides with a charge state above +4 were generated, many of which were unresolved due to overlapping species from m/z 700 to m/z 1400. From 2 to 4 minutes, these very long peptides were then cleaved into relatively shorter peptides, with the highest mass around 15 kDa. The averaged spectrum from 4 to 6 minutes showed that the enzyme digestion now generated smaller pieces with charge states ranging from +2 to +5. After 10 minutes, peptides with a charge state less than 3 became dominant.

Figure 4:
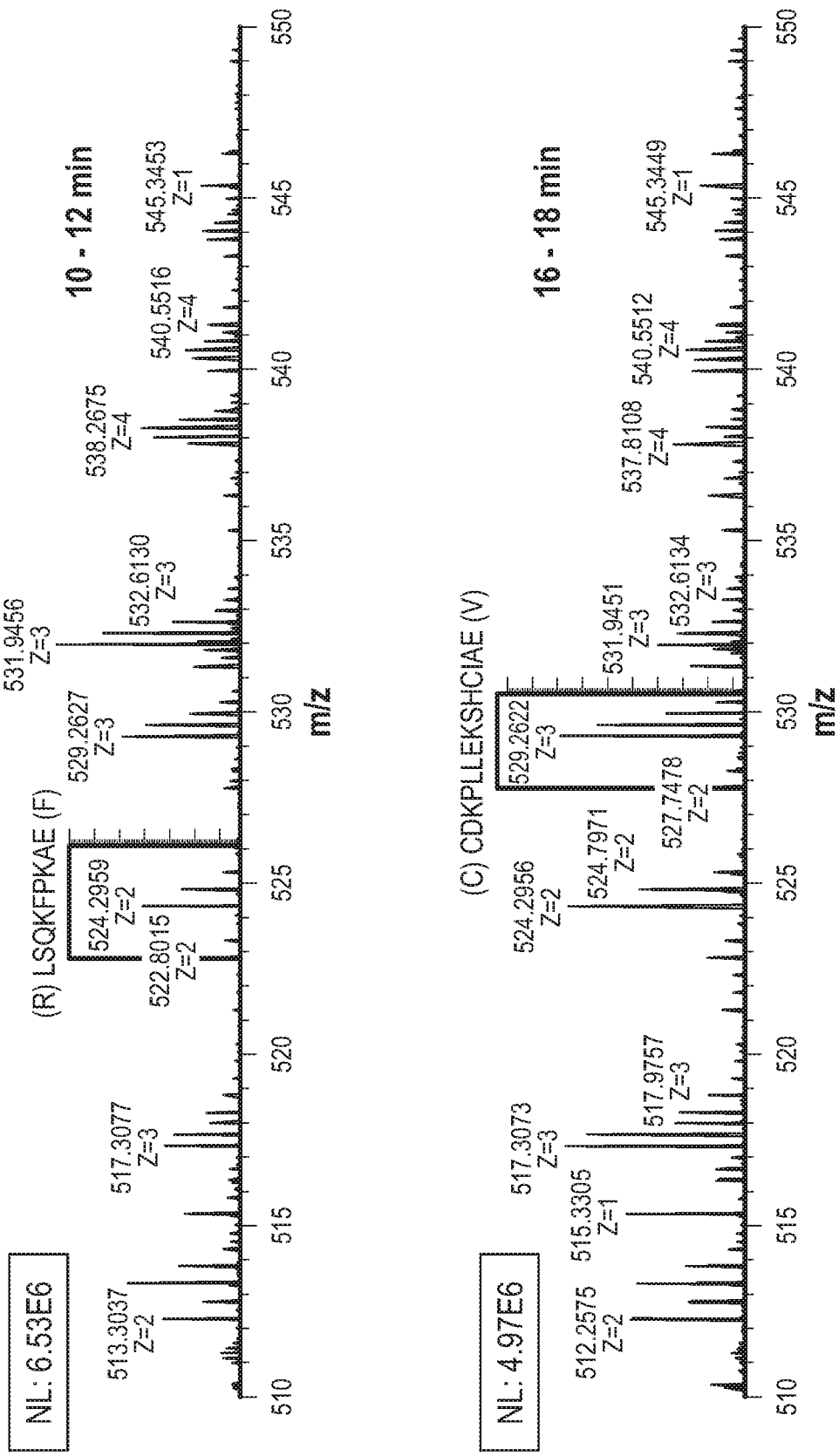
FIG. 4 shows an expanded view (m/z 500-550) of spectrum averaged over two minutes for an on-emitter protease XIII digestion of BSA carried out by the FPS method according to one exemplary embodiment.

As mass spectrometry data were acquired throughout the entire digestion process, it was questioned whether different peptides were generated with the digestion of protease XIII FIG. 4 displays the mass spectrum over the m/z 500-550 range to provide a zoomed view of peptides generated along the digestion. In the spectrum of 0 to 2 minutes, peptide CASIQKFGERALKAWSVAR (m/z 531, z=4) (SEQ ID NO: 1) is the most abundant species in that m/z range. After 2 minutes, several other peptides appeared in the spectrum; peptide VEVSRSLGKVGTRCC (SEQ ID NO: 2) now became the base peak (m/z 532, z=3). The following spectra of 4-6, 10-12, and 16-18 minutes continually demonstrated the appearance of various sets of peptides. It should be noted that the high resolution provided by Orbitrap mass analyzer unambiguously supported the peptide identification from such a complex peptide mixture.

Figure 5:
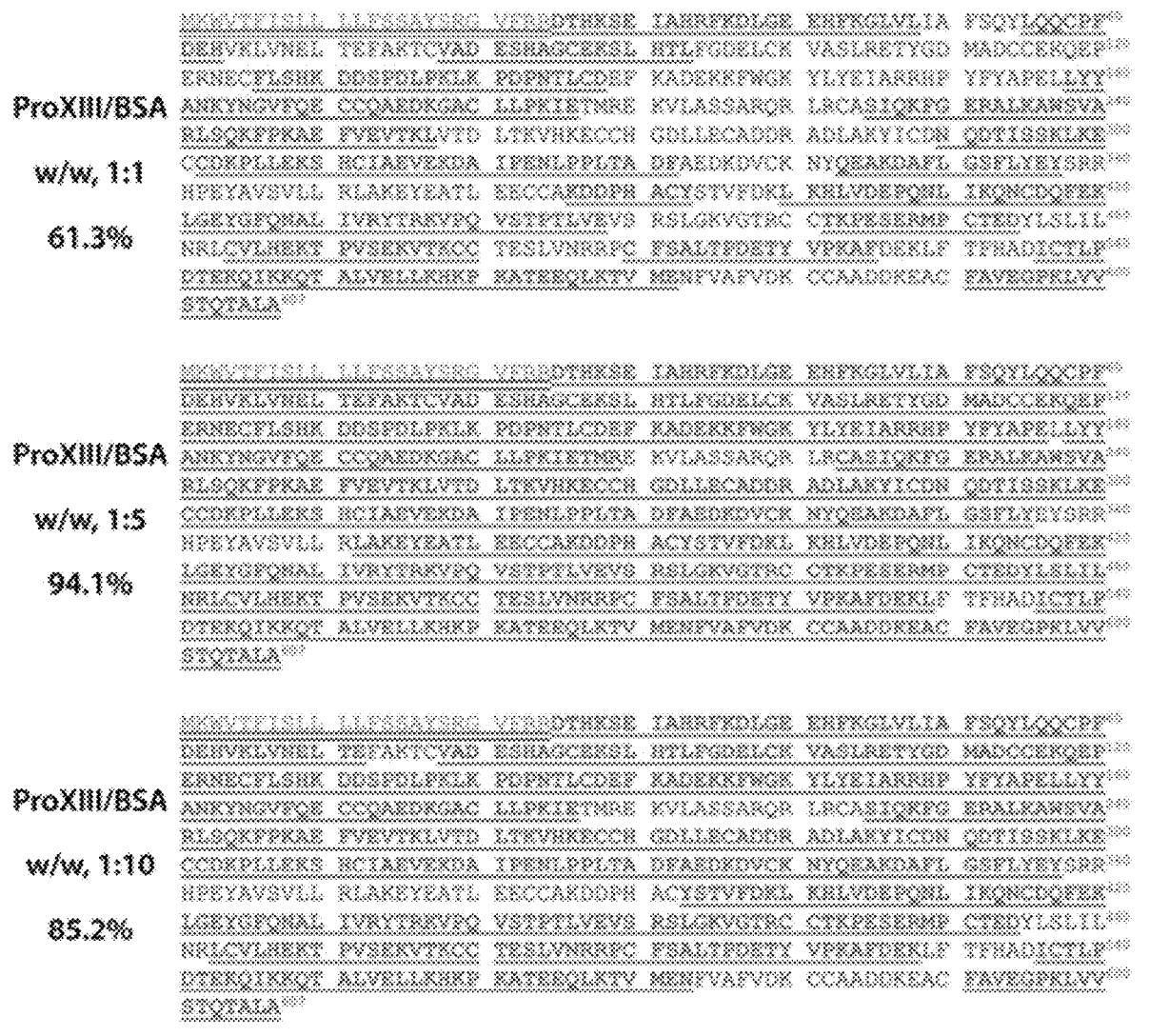

The novel experimental design and the unique enzyme cleavage pattern of protease XIII enabled obtaining the same level of protein sequence coverage as LC-MS/MS peptide mapping experiments. The many experimental conditions explored revealed that the enzyme to substrate ratio is an important factor for achieving satisfactory sequence coverage. FIG. 5 shows the resulting sequence coverage of BSA by applying the fast protein sequencing method, using 1:1, 1:5, and 1:10 E/S ratios. The experiment in which a 1:5 weight ratio of enzyme to substrate was used produced 94.1% of BSA sequence coverage, which is significantly higher than the sequence coverage of 61.3% using 1:1 and 85.2% using 1:10 E/S ratios. This suggests that it is helpful to optimize the enzyme to substrate ratio, thus the protease XIII on-emitter digestion rate, in order to achieve good sequence coverage. When the enzyme to substrate ratio is unsuitably high, the correspondingly high digestion rate may not allow sufficient time for the peptides to be analyzed by mass spectrometer, and sequence coverage may be compromised. Particularly, in this method, about twenty seconds that elapse from the step of enzyme and substrate mixing to the step of data acquisition are due to mechanical movements such as tip pickup and engagement onto the spray nozzle can compromise sequence coverage. This twenty second period may not be a problem for commonly used proteases such as trypsin or Asp-N; however, because of fast digestion by protease XIII, a considerable amount of sequence information could be lost. On the other hand, a low E/S ratio would need long digestion and thus long data acquisition time, and therefore may not accommodate the fast protein sequencing approach that is intended to limit the parallel digestion and data acquisition process to thirty minutes.

Example 2. Sequencing a Mouse Monoclonal Antibody IgG1 MOPC21 by FPS Using Protease XIII After demonstrating the effectiveness and efficiency of this method using BSA, the FPS method was used to sequence a mouse monoclonal antibody IgG1 MOPC21.

2.1 Protein Preparation.

MOPC 21 was supplied as a solution with a concentration of 1.0 mg/mL in 0.02 M Tris buffered saline, pH 8.0. MOPC21 (100 μg) was desalted with NanoSep 10K filter for 12 minutes and resuspended in 100 μL of Milli-Q water. The sample was then reduced and desalted again as described above in 1.1.

2.2 Protease XIII Preparation.

A 10 μg/μL protease XIII stock solution was made with Milli-Q water.

2.3 Direct Infusion Mass Spectrometric Analysis.

MS mass analyses were performed using a linear ion trap-Orbitrap hybrid mass spectrometer (LTQ-Orbitrap Velos, Thermo Fisher Scientific, San Jose, Calif., USA) with a TriVersa NanoMate® (Advion Biosciences, Ithaca, USA) mounted in front. The TriVersa NanoMate was operated in the infusion mode. The TriVersa NanoMate was triggered once the protein and protease XIII were mixed. The infusion mandrel picked up an infusion tip from the infusion tip box and moved to the Eppendorf plate (Protein LowBind MTP 384/V-bottom, Eppendorf, Edison, N.J., USA) to aspirate 15 μL of sample. The infusion mandrel then engaged the infusion tip to the chip and a positive voltage (1.4 kV) was applied on the carbon-coated infusion tip while the mass spectrometer sample orifice remained at 0 kV. The very intense electrostatic field between the sample in the infusion tip and the grounded outside surface of the spray nozzle on the nano ESI chip generated the electrospray. The vacuum inside the mass spectrometer drove the positive ions towards the mass spectrometer. Mass analysis was completed using a method consisting of one high resolution full MS (resolution of 60,000 at m/z 400) acquired in the orbitrap, followed by 10 data-dependent CAD scans acquired in LTQ. Data-dependence parameters were set as follows: repeat count of 1, repeat duration of 120 s, 3 m/z precursor isolation window, charge state rejection for +1 precursor ions. The raw data were searched against protein database containing IgG1 MOPC21 sequence with Proteome Discoverer 1.4 (Thermo Scientific).

2.4 Results.

Figure 6:
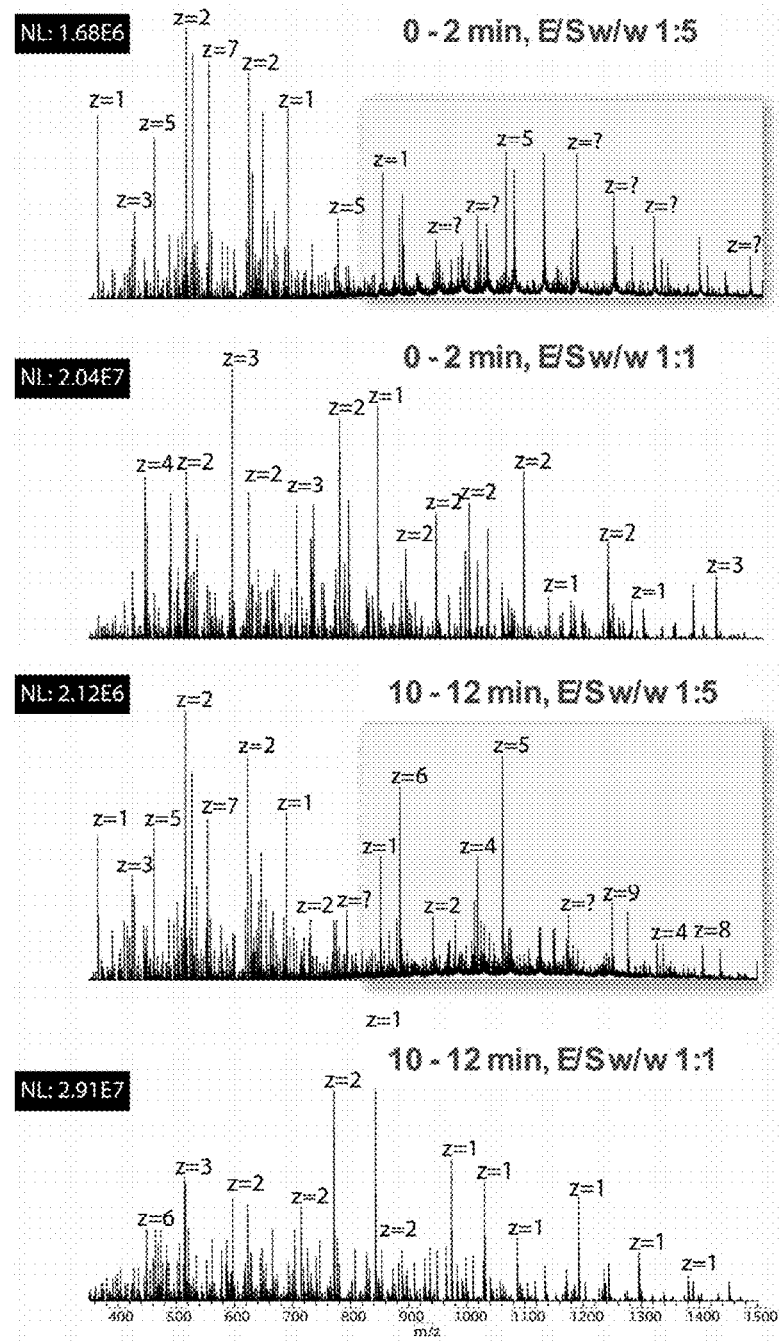
FIG. 6 shows sequencing of IgG1 MOPC21 carried out by the FPS method according to one exemplary embodiment. Each panel shows a spectrum averaged over two minutes.

On learning that the enzyme to substrate ratio is critical from the characterization of the BSA protein, the digestion patterns of MOPC21 using 1:1 and 1:5 E/S ratios were compared (FIG. 6) and an E/S ratio of 1:5 was used. Using this ratio revealed large pieces of antibody (highlighted region) in the first two minutes. There was still a significant amount of highly charged species shown in the averaged spectrum from ten to twelve minutes. When an E/S ratio of 1:1 was used, peaks with charge states less than four dominated the averaged spectrum over the first two minutes. The averaged spectrum from ten to twelve minutes contains mainly singly and doubly charged species. The data shown in FIG. 5 demonstrates an optimal E/S ratio of 1:5 for BSA may not be the most suitable for antibodies. In the case of IgG1 MOPC21, an E/S ratio of 1:1 elucidates more sequence information than an E/S ratio of 1:5. FIG. 7 shows the sequence coverage obtained with an E/S ratio of 1:1. The sequence coverage of MOPC21 heavy chain and light chain were 75.6% and 95.3%, which are much higher than the sequence coverage obtained with an E/S ratio 1:5 (data not shown). For this fast protein sequencing method, glycosylation was not included in the database search; therefore there was no coverage around the consensus sequence (marked in red) of N-glycosylation in the heavy chain CH2 constant domain. The sequence coverage of heavy chain could be higher if glycosylation is taken into consideration.

Example 3. Sequencing NIST Monoclonal Antibody (NISTmAb) by FPS Using Protease XIII 3.1 Protein Preparation.

NISTmAb was supplied as a solution with a concentration of 1.0 mg/mL in 0.02 M Tris buffered saline, pH 8.0. NISTmAb (100 μg) was desalted with NanoSep 10K filter for twelve minutes and resuspended in 100 μL of Milli-Q water. The sample was then reduced and desalted again as described above in 1.1.

3.2 Protease XIII Preparation.

A 10 μg/μL protease XIII stock solution was made with Milli-Q water.

3.3 Direct Infusion Mass Spectrometric Analysis.

Direct infusion of this experiment using NISTmAB and protease XIII was performed using the method illustrated for mouse monoclonal antibody IgG1 MOPC21 and protease XIII in 2.3.

3.4 Results.

The digestion patterns of NISTmAb were obtained using 1:1, 1:5, and 1:10 E/S ratios. The data shown in FIGS. 8, 9, and 10 demonstrates the sequence coverage for NISTmAb using 1:1 E:S ratio, E:S 1:5 ratio, and 1:10 E:S ratio, respectively. In the case of NISTmAb, an E/S ratio of 1:5 elucidates more sequence information (See FIG. 9). The sequence coverage of NISTmAb heavy chain and light chain were 93.3% and 98.6%, which are much higher than the sequence coverage obtained with an E/S ratios of 1:1 and 1:10.

Example 4. Sequencing NIST Monoclonal Antibody (NISTmAb) by FPS Using Pepsin 4.1 Protein Preparation.

NISTmAb was supplied as a solution with a concentration of 1.0 mg/mL in 0.02 M Tris buffered saline, pH 8.0. NISTmAb (100 μg) was desalted with NanoSep 10K filter for 12 minutes and resuspended in 100 μL of Milli-Q water. The sample was then reduced and desalted again as described above in 1.1.

4.2 Pepsin Preparation.

A 10 μg/μL pepsin stock solution was made with Milli-Q water.

4.3 Direct Infusion Mass Spectrometric Analysis.

Direct infusion of this experiment using NISTmAB and pepsin was performed using the method illustrated for mouse monoclonal antibody IgG1 MOPC21 and protease XIII in 2.3.

4.4 Results.

The digestion patterns of NISTmAb were obtained using 1:1, 1:5, and 1:10 E/S ratios. The data shown in FIGS. 11, 12 and 13 demonstrates the sequence coverage for NISTmAb using pepsin in 1:1 E:S ratio, E:S 1:5 ratio, and 1:10 E:S ratio, respectively. In the case of digestion of NISTmAb using pepsin, an E/S ratio of 1:10 elucidates more sequence information (See FIG. 13). The sequence coverage of NISTmAb heavy chain and light chain were 93.3% and 97.2%, which are much higher than the sequence coverage obtained with an E/S ratios of 1:1 and 1:5.

Example 5. Cleavage Preference Determination of Protease XIII Using In-Solution Protease XIII Digestion of Human Protein Extract Human protein extract solution (100 µg) was mixed with 5 mM DTT at 37° C. for 30 minutes. The reduced samples were then digested with protease XIII (1:1 w/w enzyme:substrate ratio) at room temperature for 10 minutes. The sample was then immediately injected into an EASY-nLC 1000 system (Thermo Fisher Scientific) coupled with a Q Exactive Plus Orbitrap mass spectrometer (Thermo Fisher Scientific, Bremen, Germany) for LC-MS/MS analysis.

5.1 NanoLC Mass Spectrometric Analysis.

For peptide separation and identification, peptide mixture generated by protease XIII digestion was loaded onto a reverse phase trap column (2 cm×75 µm, 5 µm) and then eluted to the C18-reversed phase analytical column (15 cm×75 µm, 3 µm) for the separation. Buffer A (0.1% formic acid in water) was used for equilibration of chromatographic columns, and buffer B (0.1% formic acid in acetonitrile), with a linear gradient at a flow rate of 300 nL/min, was utilized for mixture separation. The peptides were subjected to a nano-electrospray ionization followed by HCD MS/MS in a Q-Exactive Plus mass spectrometer coupled to Easy nLC. The mass spectrometer was operated in positive-ion detection mode. A Full MS scan was acquired in the Orbitrap mass analyzer over an m/z range of 400-2000 at a resolution of 70,000 (at m/z 200). The ten most abundant ion peaks with charge state≥2 were fragmented in the HCD collision cell with normalized collision energy of 27% for each full scan cycle, and tandem mass spectrum was acquired in the Orbitrap mass analyzer with a resolution of 17,000 (at m/z 200). The automatic gain control targets were set to 1.0E+06 for full MS scan and 1.0E+05 for MS/MS scan. The underfill ratio was defined as 0.1%, and the maximum allowed ion accumulation times were 50 ms for full MS scans and 100 ms for tandem mass spectrum. The dynamic exclusion was set to 15 s.

5.2 Data Analysis.

Database search of protease XIII digested human protein extract LC-MS/MS raw data was performed using SEQUEST embedded into Proteome Discoverer 1.4 (Thermo Fisher Scientific) against the Uniprot human protein database. The search parameters were: 15 ppm tolerance for precursor ion masses, 0.02 Da tolerance for fragment ion masses analyzed by Orbitrap. No enzyme was specified during the database search. Methionine oxidation (+16 Da) was set as a variable modification. The false discovery rate (FDR) was determined by using the target-decoy strategy and was set to 1% for peptide identification (Elias et al. "Comparative evaluation of mass spectrometry platforms used in large-scale proteomics investigations" Nat. Methods. (2005) 2: 667-75).

5.3 Results.

Figure 14:
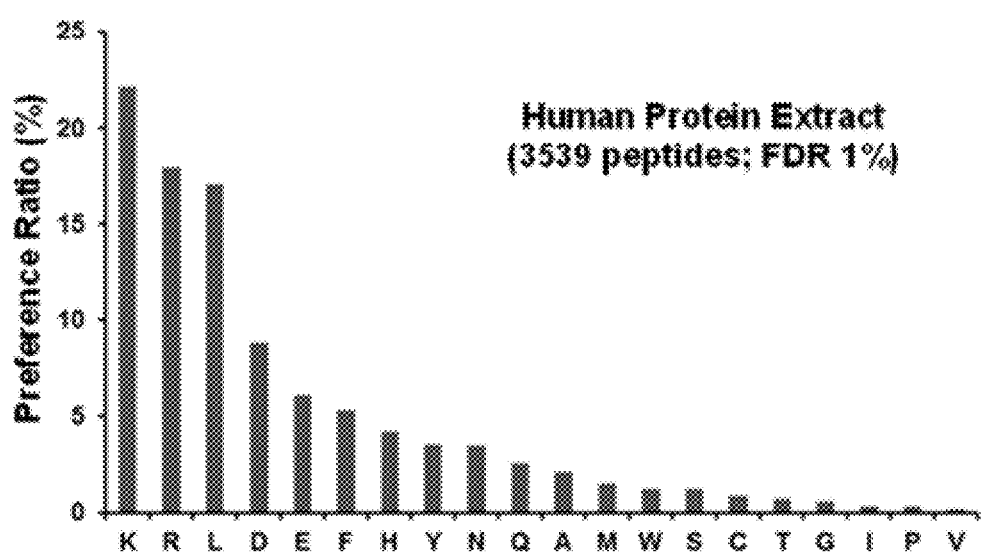
FIG. 14 shows the Protease XIII cleavage preference for various amino acids. The protease XIII cleavage preference for each amino acid residue is calculated as $n_1/n_2$, where $n_1$ is the number of each cleaved residue, and $n_2$ is the total number of all cleaved residues identified in the protease XIII digestion of human protein extracts. The false discovery rate (FDR) was set to 1% for peptide identification.

Cleavage preference for a protease can be determined based on the ratio of the number of a particular amino acid as the site of cleavage to the total number of cleaved amino acids in the protein sequences. FIG. 14 shows the cleavage preferences of protease XIII on human protein extracts. For the statistical analysis on 3,539 peptides in this study, a stronger preference of protease type XIII to cleave at the C-terminal of two basic amino acid residues (i.e., lysine and arginine residues) and one neutral amino acid residue (i.e., leucine residue) compared to other amino acid residues, was observed. This observation is similar to that reported by Zhang et al. (Zhang et al. "Enhanced digestion efficiency, peptide ionization efficiency, and sequence resolution for protein hydrogen/deuterium exchange monitored by FT-ICR mass spectrometry" Anal. Chem. (2008) 80: 9034-41). A lower preference of protease XIII to cleave at the C-terminal of isoleucine compared with leucine (Ile 0.3% vs. Leu 17% in terms of preference ratio) was observed. This was interesting given that the amino acid abundance of leucine is only twice as much as that of isoleucine (see Switzar (2013), supra). Poston et al. developed a set of orthogonal biochemical protocols to experimentally determine the identity of Ile or Leu residue isomer for de novo sequencing of monoclonal antibodies based on the selectivity that leucine aminopeptidase shows for N-terminal Leu residue and the cleavage preference for Leu by chymotrypsin (Poston et al. "A quantitative tool to distinguish isobaric leucine and isoleucine residues for mass spectrometry-based de novo monoclonal antibody sequencing" J. Am. Soc. Mass Spectrom. (2014) 25: 1228-36). This finding demonstrates that the protease type XIII could be considered as a potential leucine-specific protease to differentiate Leu from Ile residue for protein de novo sequencing.

Compared with commonly used proteases such as trypsin or AspN, protease XIII showed a low specificity (FIG. 14). This nature of non-specific cleavage can be essential for producing a substantial amount of overlapping peptides, which is important for obtaining good sequence coverage. As there is no LC-timescale of separation, the vast number of peptides generated during the digestion may lead to a crowded spectrum, which makes the isolation of precursor ion a challenging task. For example, in FIG. 4, in the first two minutes a +4 peptide, CASIQKFGERALKAWSVAR (SEQ ID NO:1), was the base peak in the expanded m/z range. Two minutes later, a +3 peptide, VEVSRSLGKVGTRCC (SEQ ID NO: 2), showed up on the right of the peptide, CASIQKFGERALKAWSVAR (SEQ ID NO: 1). The m/z values of these two peptides are very close to each other. With a standard precursor isolation width, these two peptides could be co-isolated, and thus a mixed CAD spectrum can be generated. There was an initial concern about the possibility of a mixed spectrum interfering with peptide identification. However, during the experiment, it was found that most of the time, the mass spectrometer was able to isolate the precursor while its vicinity is relatively free of contaminant ions. Using the same example presented in FIG. 3, when the digestion continued to four to six minutes, the +4 peptide, CASIQKFGERALKAWSVAR (SEQ ID NO: 1), was almost fully digested and the +3 peptide, VEVSRSLGKVGTRCC (SEQ ID NO: 2), became the base peak. Thus, the +3 peptide can be isolated with high purity, generating a clean CAD spectrum for the peptide identification.

Compared to the traditional bottom-up protein sequencing approach, the FPS method offers several unique advantages. The sample preparation and instrument operation procedures are simple to follow, and protein reduction and desalting takes 20-30 minutes. As digestion occurred on the spray emitter, significant amounts of disulfide bond reforming after reduction were not observed; hence alkylation step was removed from this method. However, most of the efficiency of the FPS method results from the fast digestion rate by protease XIII and the novel design of having the digestion on a spray emitter and acquiring mass spectrometry data in parallel to digestion. As a result, the duration of digestion and mass spectrometry data acquisition was reduced from eight to twenty hours to less than half an hour. Due to the real-time monitoring nature of the protein digestion, it offers a unique view on regions along the protein amino acid sequence that are most susceptible to enzyme digestion. Although the FPS method could be implemented on any nanospray infusion setup, using the direct infusion mode of Advion TriVersa NanoMate® highly simplified workflow, enhanced the level of automation, and strengthened the robustness of this approach. In this study, a workflow with a 30-minute data acquisition was developed; however, it is possible to achieve the same sequence coverage in a shorter period. As shown in FIG. 2, peptides with +1 to +3 charge state were dominant during the period of 16-18 minutes. Further digestion reduced the charge states of +2 and +3 to +1 does not produce good MS/MS spectra for sequencing and therefore cannot improve sequence coverage.

As recombinant monoclonal antibodies contain substantially conserved conformation and amino acid sequence, the optimized E/S ratio of 1:1 in the work on IgG1 MOPC21 could be used to guide the sequencing of other proteins using the FPS method. Besides E/S ratio, pH and temperature can also alter the digestion rate by affecting the enzymatic activity. In the experiments, the digestion/electrospray buffer was Milli-Q water; the digestion occurred on the infusion tip which was engaged to the spray nozzle. The nozzle is a few millimeters away from the mass spectrometer ion transfer tube, which was heated at 350° C. It has been reported by several groups that an optimized digestion condition for protease XIII after a H/D exchange experiment was pH 2.3-2.5 at 0° C. for 2 minutes, which suggests that protease XIII has a high tolerance for pH and can still be active at a pH as low as 2-3 (see Zhang et al. (2008), supra and Cravello et al. (2003), supra). Although protease XIII is generally categorized as a non-specific protease, the data showed that this enzyme prefers to cleave on the C-terminal side of basic amino acids and interestingly leucine amino acid residue (FIG. 14). This facilitates the generation of peptides that may become highly charged under positive ESI therefore enhancing ionization efficiency and benefiting the following MS/MS fragmentation (see Zhang et al. (2008), supra and Cravello et al. (2003), supra). This also provides a protease-specificity based approach for the distinction of leucine from isoleucine in the protein de novo sequencing.

What is claimed is:

1. A method of analyzing at least one protein in a sample, said method comprising:
   mixing a protease enzyme with said sample to form a final sample;
   contacting the final sample to an electrospray emitter; and
   analyzing the final sample using a tandem mass spectrometry, wherein digestion of the at least one protein by the protease enzyme occurs on the electrospray emitter and wherein the digestion is monitored in real time.

2. The method of claim 1, wherein the at least one protein is denatured.

3. The method of claim 2, wherein the at least one protein is denatured before contacting to the electrospray emitter.

4. The method of claim 1, wherein the at least one protein is reduced.

5. The method of claim 1, wherein the at least one protein is desalted.

6. The method of claim 1, wherein the at least one protein is an antibody.

7. The method of claim 6, wherein the antibody is a monoclonal antibody.

8. The method of claim 6, wherein the antibody is a therapeutic antibody.

9. The method of claim 6, wherein the antibody is an NIST monoclonal antibody.

10. The method of claim 6, wherein the antibody is MOPC-21 antibody.

11. The method of claim 1, wherein the at least one protein is a globular protein.

12. The method of claim 1, wherein weight ratio of the protease enzyme to the at least one protein in the final sample is about 1:1 to about 1:10.

13. The method of claim 1, wherein weight ratio of the protease enzyme to the at least one protein in the final sample is about 1:5.

14. The method of claim 1, wherein concentration of the at least one protein in the sample is less than about 10 µg/µL.

15. The method of claim 1, wherein concentration of the at least one protein in the sample is about 1 µg/µL.

16. The method of claim 1, further comprising aspirating the final sample.

17. The method of claim 1, wherein the tandem mass spectrometry uses a positive voltage.

18. The method of claim 1, wherein a period of time to analyze the final sample is less than about an hour.

19. The method of claim 1, wherein the protease enzyme is a non-specific protease.

20. The method of claim 1, wherein the protease enzyme is from *Aspergillus* saitoi.

21. The method of claim 1, wherein the protease enzyme has a greater preference to cleave at C-terminal versus the N-terminal of an amino-acid residue.

22. The method of claim 21, wherein the amino-acid residue is arginine, lysine, or leucine.

23. The method of claim 1, wherein the protease enzyme is protease XIII.

24. The method of claim 1, wherein the protease enzyme is pepsin.

25. The method of claim 1, wherein the final sample contacts an electrospray ionization chip.

26. A method of sequencing at least one protein in a sample, said method comprising:
    mixing a protease enzyme with said sample to form a final sample;
    contacting the final sample to an electrospray emitter; and
    analyzing the final sample using a tandem mass spectrometry, wherein digestion of the at least one protein by the protease enzyme occurs on the electrospray emitter and wherein the digestion is monitored in real time.

27. A method of characterizing at least one protein in a sample, said method comprising:
    mixing a protease enzyme with said sample to form a final sample;
    contacting the final sample to an electrospray emitter; and
    analyzing the final sample using a tandem mass spectrometry, wherein digestion of the at least one protein by the protease enzyme occurs on the electrospray emitter and wherein the digestion is monitored in real time.

28. A method of claim 27, wherein the method includes protein sequencing, protein de novo sequencing, or identifying post translational modifications, or comparability analysis, or combinations thereof.

* * * * *

SEQUENCE LISTING

```
<160> NUMBER OF SEQ ID NOS: 12

<210> SEQ ID NO 1
<211> LENGTH: 19
<212> TYPE: PRT
<213> ORGANISM: Bos taurus

<400> SEQUENCE: 1

Cys Ala Ser Ile Gln Lys Phe Gly Glu Arg Ala Leu Lys Ala Trp Ser
1               5                   10                  15

Val Ala Arg

<210> SEQ ID NO 2
<211> LENGTH: 15
<212> TYPE: PRT
<213> ORGANISM: Bos taurus

<400> SEQUENCE: 2

Val Glu Val Ser Arg Ser Leu Gly Lys Val Gly Thr Arg Cys Cys
1               5                   10                  15

<210> SEQ ID NO 3
<211> LENGTH: 21
<212> TYPE: PRT
<213> ORGANISM: Bos taurus

<400> SEQUENCE: 3

Arg Cys Ala Ser Ile Gln Lys Phe Gly Glu Arg Ala Leu Lys Ala Trp
1               5                   10                  15

Ser Val Ala Arg Leu
                20

<210> SEQ ID NO 4
<211> LENGTH: 20
<212> TYPE: PRT
<213> ORGANISM: Bos taurus

<400> SEQUENCE: 4

Arg Asp Thr His Lys Ser Glu Ile Ala His Arg Phe Lys Asp Leu Gly
1               5                   10                  15
```

Glu Glu His Phe
            20

<210> SEQ ID NO 5
<211> LENGTH: 17
<212> TYPE: PRT
<213> ORGANISM: Bos taurus

<400> SEQUENCE: 5

Leu Val Glu Val Ser Arg Ser Leu Gly Lys Val Gly Thr Arg Cys Cys
1               5                   10                  15

Thr

<210> SEQ ID NO 6
<211> LENGTH: 11
<212> TYPE: PRT
<213> ORGANISM: Bos taurus

<400> SEQUENCE: 6

Arg Leu Ser Gln Lys Phe Pro Lys Ala Glu Phe
1               5                   10

<210> SEQ ID NO 7
<211> LENGTH: 16
<212> TYPE: PRT
<213> ORGANISM: Bos taurus

<400> SEQUENCE: 7

Cys Cys Asp Lys Pro Leu Leu Glu Lys Ser His Cys Ile Ala Glu Val
1               5                   10                  15

<210> SEQ ID NO 8
<211> LENGTH: 607
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Lys Trp Val Thr Phe Ile Ser Leu Leu Leu Leu Phe Ser Ser Ala
1               5                   10                  15

Tyr Ser Arg Gly Val Phe Arg Arg Asp Thr His Lys Ser Glu Ile Ala
                20                  25                  30

His Arg Phe Lys Asp Leu Gly Glu Glu His Phe Lys Gly Leu Val Leu
            35                  40                  45

Ile Ala Phe Ser Gln Tyr Leu Gln Gln Cys Pro Phe Asp Glu His Val
        50                  55                  60

Lys Leu Val Asn Glu Leu Thr Glu Phe Ala Lys Thr Cys Val Ala Asp
65                  70                  75                  80

Glu Ser His Ala Gly Cys Glu Lys Ser Leu His Thr Leu Phe Gly Asp
                85                  90                  95

Glu Leu Cys Lys Val Ala Ser Leu Arg Glu Thr Tyr Gly Asp Met Ala
            100                 105                 110

Asp Cys Cys Glu Lys Gln Glu Pro Glu Arg Asn Glu Cys Phe Leu Ser
        115                 120                 125

His Lys Asp Asp Ser Pro Asp Leu Pro Lys Leu Lys Pro Asp Pro Asn
    130                 135                 140

Thr Leu Cys Asp Glu Phe Lys Ala Asp Glu Lys Lys Phe Trp Gly Lys
145                 150                 155                 160

```
Tyr Leu Tyr Glu Ile Ala Arg Arg His Pro Tyr Phe Tyr Ala Pro Glu
            165                 170                 175

Leu Leu Tyr Tyr Ala Asn Lys Tyr Asn Gly Val Phe Gln Glu Cys Cys
            180                 185                 190

Gln Ala Glu Asp Lys Gly Ala Cys Leu Leu Pro Lys Ile Glu Thr Met
            195                 200                 205

Arg Glu Lys Val Leu Ala Ser Ser Ala Arg Gln Arg Leu Arg Cys Ala
            210                 215                 220

Ser Ile Gln Lys Phe Gly Glu Arg Ala Leu Lys Ala Trp Ser Val Ala
225                 230                 235                 240

Arg Leu Ser Gln Lys Phe Pro Lys Ala Glu Phe Val Glu Val Thr Lys
            245                 250                 255

Leu Val Thr Asp Leu Thr Lys Val His Lys Glu Cys Cys His Gly Asp
            260                 265                 270

Leu Leu Glu Cys Ala Asp Asp Arg Ala Asp Leu Ala Lys Tyr Ile Cys
            275                 280                 285

Asp Asn Gln Asp Thr Ile Ser Ser Lys Leu Lys Glu Cys Cys Asp Lys
            290                 295                 300

Pro Leu Leu Glu Lys Ser His Cys Ile Ala Glu Val Glu Lys Asp Ala
305                 310                 315                 320

Ile Pro Glu Asn Leu Pro Pro Leu Thr Ala Asp Phe Ala Glu Asp Lys
            325                 330                 335

Asp Val Cys Lys Asn Tyr Gln Glu Ala Lys Asp Ala Phe Leu Gly Ser
            340                 345                 350

Phe Leu Tyr Glu Tyr Ser Arg Arg His Pro Glu Tyr Ala Val Ser Val
            355                 360                 365

Leu Leu Arg Leu Ala Lys Glu Tyr Glu Ala Thr Leu Glu Glu Cys Cys
            370                 375                 380

Ala Lys Asp Asp Pro His Ala Cys Tyr Ser Thr Val Phe Asp Lys Leu
385                 390                 395                 400

Lys His Leu Val Asp Glu Pro Gln Asn Leu Ile Lys Gln Asn Cys Asp
            405                 410                 415

Gln Phe Glu Lys Leu Gly Glu Tyr Gly Phe Gln Asn Ala Leu Ile Val
            420                 425                 430

Arg Tyr Thr Arg Lys Val Pro Gln Val Ser Thr Pro Thr Leu Val Glu
            435                 440                 445

Val Ser Arg Ser Leu Gly Lys Val Gly Thr Arg Cys Cys Thr Lys Pro
450                 455                 460

Glu Ser Glu Arg Met Pro Cys Thr Glu Asp Tyr Leu Ser Leu Ile Leu
465                 470                 475                 480

Asn Arg Leu Cys Val Leu His Glu Lys Thr Pro Val Ser Glu Lys Val
            485                 490                 495

Thr Lys Cys Cys Thr Glu Ser Leu Val Asn Arg Arg Pro Cys Phe Ser
            500                 505                 510

Ala Leu Thr Pro Asp Glu Thr Tyr Val Pro Lys Ala Phe Asp Glu Lys
            515                 520                 525

Leu Phe Thr Phe His Ala Asp Ile Cys Thr Leu Pro Asp Thr Glu Lys
            530                 535                 540

Gln Ile Lys Lys Gln Thr Ala Leu Val Glu Leu Leu Lys His Lys Pro
545                 550                 555                 560

Lys Ala Thr Glu Glu Gln Leu Lys Thr Val Met Glu Asn Phe Val Ala
            565                 570                 575
```

```
Phe Val Asp Lys Cys Cys Ala Ala Asp Asp Lys Glu Ala Cys Phe Ala
                580                 585                 590

Val Glu Gly Pro Lys Leu Val Ser Thr Gln Thr Ala Leu Ala
        595                 600                 605

<210> SEQ ID NO 9
<211> LENGTH: 442
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Leu His Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Trp Gly Asn Tyr Pro Tyr Tyr Ala Met Asp Tyr Trp Gly Gln
            100                 105                 110

Gly Thr Ser Val Thr Val Ser Ser Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
            180                 185                 190

Ser Thr Trp Pro Ser Glu Thr Val Thr Cys Asn Val Ala His Pro Ala
        195                 200                 205

Ser Ser Thr Lys Val Asp Lys Lys Ile Val Pro Arg Asp Cys Gly Cys
    210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Gln Pro
        275                 280                 285

Arg Glu Glu Gln Phe Asn Ser Thr Phe Arg Ser Val Ser Glu Leu Pro
    290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335
```

```
Lys Gly Arg Pro Lys Ala Pro Gln Val Tyr Thr Pro Pro Lys Glu
            340                 345                 350

Gln Met Ala Lys Asp Lys Val Ser Leu Thr Cys Met Ile Thr Asp Phe
        355                 360                 365

Phe Pro Glu Asp Ile Thr Val Glu Trp Gln Trp Asn Gly Gln Pro Ala
    370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu Glu Asn His His
                420                 425                 430

Thr Glu Lys Ser Leu Ser His Ser Pro Gly
                435                 440
```

<210> SEQ ID NO 10
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Asn Ile Val Met Thr Gln Ser Pro Lys Ser Met Ser Met Ser Val Gly
1               5                   10                  15

Glu Arg Val Thr Leu Thr Cys Lys Ala Ser Glu Asn Val Val Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Gly Tyr Ser Tyr Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210
```

<210> SEQ ID NO 11
<211> LENGTH: 450
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 11

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys His Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Phe Tyr Phe Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380
```

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 12
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```